(12) United States Patent
Miller et al.

(10) Patent No.: US 9,757,464 B2
(45) Date of Patent: *Sep. 12, 2017

(54) PHARMACEUTICAL COMPOSITIONS OF DEXTRAN POLYMER DERIVATIVES

(71) Applicant: Bend Research, Inc., Bend, OR (US)

(72) Inventors: Warren K. Miller, Bend, OR (US);
David T. Vodak, Bend, OR (US);
Daniel E. Dobry, Bend, OR (US);
David K. Lyon, Bend, OR (US);
Dwayne T. Friesen, Bend, OR (US);
Michael M. Morgen, Bend, OR (US);
Corey J. Bloom, Bend, OR (US);
Daniel T. Smithey, Bend, OR (US)

(73) Assignee: Bend Research, Inc., Bend, OR (US)

( * ) Notice: Subject to any disclaimer, the term of this patent is extended or adjusted under 35 U.S.C. 154(b) by 388 days.

This patent is subject to a terminal disclaimer.

(21) Appl. No.: 14/179,480

(22) Filed: Feb. 12, 2014

(65) Prior Publication Data

US 2014/0161895 A1    Jun. 12, 2014

Related U.S. Application Data

(63) Continuation of application No. 13/254,802, filed as application No. PCT/US2010/026127 on Mar. 3, 2010, now Pat. No. 8,685,458.

(60) Provisional application No. 61/157,854, filed on Mar. 5, 2009, provisional application No. 61/178,690, filed on May 15, 2009.

(51) Int. Cl.
| | |
|---|---|
| *A61K 47/36* | (2006.01) |
| *A61K 9/00* | (2006.01) |
| *A61K 9/10* | (2006.01) |
| *A61K 9/16* | (2006.01) |
| *A61K 9/19* | (2006.01) |
| *A61K 9/51* | (2006.01) |
| *A61K 31/57* | (2006.01) |

(52) U.S. Cl.
CPC ............ *A61K 47/36* (2013.01); *A61K 9/0019* (2013.01); *A61K 9/0048* (2013.01); *A61K 9/0075* (2013.01); *A61K 9/0095* (2013.01); *A61K 9/10* (2013.01); *A61K 9/1652* (2013.01); *A61K 9/19* (2013.01); *A61K 9/5161* (2013.01); *A61K 31/57* (2013.01)

(58) Field of Classification Search
None
See application file for complete search history.

(56) References Cited

U.S. PATENT DOCUMENTS

| | | | |
|---|---|---|---|
| 2,196,768 A * | 4/1940 | Hiatt | A61K 9/4816 424/459 |
| 4,451,452 A | 5/1984 | Deibig et al. | |
| 4,501,726 A | 2/1985 | Schröder et al. | |
| 4,615,881 A * | 10/1986 | Deibig | A61K 9/1635 514/1.7 |
| 4,713,249 A | 12/1987 | Schröder | |
| 5,688,931 A | 11/1997 | Nogusa et al. | |
| 5,744,153 A | 4/1998 | Yewey et al. | |
| 5,759,563 A | 6/1998 | Yewey et al. | |
| 5,780,044 A | 7/1998 | Yewey et al. | |
| 5,792,475 A | 8/1998 | Davis et al. | |
| 5,928,669 A | 7/1999 | Davis et al. | |
| 5,981,719 A | 11/1999 | Woiszwillo et al. | |
| 6,048,515 A | 4/2000 | Kresse et al. | |
| 6,090,925 A | 7/2000 | Woiszwillo et al. | |
| 6,165,506 A | 12/2000 | Jain et al. | |
| RE37,053 E | 2/2001 | Hanes et al. | |
| 6,200,590 B1 | 3/2001 | Eley | |
| 6,268,053 B1 | 7/2001 | Woiszwillo et al. | |
| 6,303,148 B1 | 10/2001 | Hennink et al. | |
| 6,395,302 B1 | 5/2002 | Hennink et al. | |
| 6,497,903 B1 | 12/2002 | Hennink et al. | |
| 6,541,039 B1 | 4/2003 | Lesniak et al. | |
| 6,576,221 B1 | 6/2003 | Kresse et al. | |
| 6,589,557 B2 | 7/2003 | Straub et al. | |
| 6,589,562 B1 | 7/2003 | Shefer et al. | |
| 6,610,317 B2 | 8/2003 | Straub et al. | |
| 6,632,671 B2 | 10/2003 | Unger | |
| 6,685,927 B2 | 2/2004 | Sumian et al. | |
| 6,740,631 B2 | 5/2004 | Shefer et al. | |
| 6,800,297 B2 | 10/2004 | Altreuter et al. | |
| 6,825,161 B2 | 11/2004 | Shefer et al. | |

(Continued)

FOREIGN PATENT DOCUMENTS

| | | |
|---|---|---|
| DE | 41 36 324 A1 | 5/1993 |
| DE | 42 08 946 A1 | 9/1993 |

(Continued)

OTHER PUBLICATIONS

US 5,849,884, 12/1998, Woiszwillo et al. (withdrawn)
International Search Report and Written Opinion, dated Feb. 22, 2011, issued in related International Application No. PCT/US2010/056515.
International Search Report and Written Opinion, dated Dec. 6, 2011, issued in related International Application No. PCT/2011/040222.
Chow, et al., "Particle Engineering for Pulmonary Drug Delivery," *Phamaceutical Research*, vol. 24, No. 3, pp. 411-437 (Mar. 2007).
Cruz, et al., "Peptide Synthesis Containing a B-Cell and a T-Cell Epitope on Dextran Beads and Evaluation of Humoral Response Against Bead-Peptide Construct," *Letters in Peptide Science*, 7: 229-237, 2000.

(Continued)

*Primary Examiner* — Isaac Shomer
*Assistant Examiner* — Michael P Cohen
(74) *Attorney, Agent, or Firm* — Klarquist Sparkman, LLP

(57) ABSTRACT

Pharmaceutical compositions are provided comprising an active agent and a dextran polymer derivative. The compositions include from 0.01 to 99 wt % of an active agent and from 1 to 99.99 wt % of a dextran polymer derivative. The dextran polymer derivative is selected from dextran acetate, dextran propionate, dextran succinate, dextran acetate propionate, dextran acetate succinate, dextran propionate succinate, dextran acetate propionate succinate, and mixtures thereof.

18 Claims, 1 Drawing Sheet

(56) References Cited

U.S. PATENT DOCUMENTS

| | | | |
|---|---|---|---|
| 6,835,389 B1 | 12/2004 | Dohi et al. | |
| 6,887,493 B2 | 5/2005 | Shefer et al. | |
| 6,932,983 B1 | 8/2005 | Straub et al. | |
| 6,979,466 B2 | 12/2005 | Lesniak et al. | |
| 6,998,393 B2 | 2/2006 | Jin et al. | |
| 7,060,296 B2 | 6/2006 | Hennink et al. | |
| 7,087,246 B2 | 8/2006 | Kim et al. | |
| 7,163,700 B2 | 1/2007 | Bogue | |
| 7,300,919 B2 | 11/2007 | Patton | |
| 7,378,110 B2 | 5/2008 | Truong Le et al. | |
| 7,468,151 B2 | 12/2008 | van Buitenen et al. | |
| 7,521,069 B2 | 4/2009 | Patton et al. | |
| 7,541,022 B2 | 6/2009 | Staniforth et al. | |
| 7,625,865 B2 | 12/2009 | Colombo et al. | |
| 7,928,089 B2 | 4/2011 | Morton et al. | |
| 8,685,458 B2 * | 4/2014 | Miller | A61K 9/0019 424/489 |
| 8,815,294 B2 * | 8/2014 | Friesen | A61K 9/0075 424/489 |
| 2002/0076443 A1 | 6/2002 | Stein et al. | |
| 2002/0141943 A1 | 10/2002 | Kresse et al. | |
| 2003/0026843 A1 | 2/2003 | Bogue | |
| 2003/0054037 A1 * | 3/2003 | Babcock | A61K 9/143 424/486 |
| 2003/0118514 A1 | 6/2003 | Larhrib et al. | |
| 2003/0207776 A1 | 11/2003 | Shefer et al. | |
| 2004/0062778 A1 | 4/2004 | Shefer et al. | |
| 2004/0091535 A1 | 5/2004 | Vachon et al. | |
| 2004/0105821 A1 | 6/2004 | Bernstein et al. | |
| 2004/0109894 A1 | 6/2004 | Shefer et al. | |
| 2004/0137071 A1 | 7/2004 | Unger | |
| 2004/0176391 A1 | 9/2004 | Weers et al. | |
| 2004/0184995 A1 | 9/2004 | Katsuma et al. | |
| 2004/0224019 A1 | 11/2004 | Shefer et al. | |
| 2005/0058710 A1 | 3/2005 | Straub et al. | |
| 2005/0065047 A1 | 3/2005 | Shefer et al. | |
| 2005/0112235 A1 | 5/2005 | Shefer et al. | |
| 2005/0181059 A1 | 8/2005 | Jacob et al. | |
| 2005/0191246 A1 | 9/2005 | Bechtold-Peters et al. | |
| 2005/0238716 A1 | 10/2005 | Verrijk et al. | |
| 2005/0250881 A1 | 11/2005 | Gref et al. | |
| 2006/0025355 A1 | 2/2006 | Duddu et al. | |
| 2006/0039985 A1 | 2/2006 | Bennett et al. | |
| 2006/0110462 A1 | 5/2006 | Papadopoulos et al. | |
| 2006/0121121 A1 | 6/2006 | Jin et al. | |
| 2006/0127480 A1 | 6/2006 | Tobyn et al. | |
| 2006/0141029 A1 | 6/2006 | Heller et al. | |
| 2006/0141047 A1 | 6/2006 | Heller et al. | |
| 2006/0141075 A1 | 6/2006 | Talbot | |
| 2006/0204582 A1 | 9/2006 | Stein et al. | |
| 2006/0246142 A1 | 11/2006 | Liversidge et al. | |
| 2007/0003615 A1 | 1/2007 | Jenkins et al. | |
| 2007/0003628 A1 | 1/2007 | Liversidge et al. | |
| 2007/0015719 A1 | 1/2007 | Jenkins et al. | |
| 2007/0031490 A1 | 2/2007 | Loebenberg et al. | |
| 2007/0042049 A1 | 2/2007 | Liversidge et al. | |
| 2007/0104792 A1 | 5/2007 | Jenkins | |
| 2007/0134339 A1 | 6/2007 | Jenkins et al. | |
| 2007/0134341 A1 | 6/2007 | Kipp et al. | |
| 2007/0148100 A1 | 6/2007 | Jenkins | |
| 2007/0148236 A1 | 6/2007 | Babcock et al. | |
| 2007/0178051 A1 | 8/2007 | Pruitt et al. | |
| 2008/0057003 A1 | 3/2008 | Bechtold-Peters et al. | |
| 2008/0152585 A1 | 6/2008 | Ryde et al. | |
| 2008/0213374 A1 | 9/2008 | Carty et al. | |
| 2008/0220074 A1 | 9/2008 | Bosch et al. | |
| 2008/0234227 A1 | 9/2008 | Soula et al. | |
| 2008/0241267 A1 | 10/2008 | Verrijk | |
| 2008/0292707 A1 | 11/2008 | Babcock et al. | |
| 2009/0047336 A1 | 2/2009 | Yang et al. | |
| 2009/0181100 A1 | 7/2009 | Bosch et al. | |
| 2009/0238867 A1 | 9/2009 | Jenkins et al. | |
| 2009/0269396 A1 | 10/2009 | Cipolla et al. | |
| 2009/0274765 A1 | 11/2009 | Beduneau et al. | |
| 2010/0081956 A1 | 4/2010 | Hyde et al. | |

FOREIGN PATENT DOCUMENTS

| | | | |
|---|---|---|---|
| EP | 0051707 | 5/1982 | |
| EP | 0053580 | 6/1982 | |
| EP | 0842657 | 5/1998 | |
| EP | 0914832 | 5/1999 | |
| EP | 1184032 | 3/2002 | |
| EP | 1371364 | 12/2003 | |
| EP | 1393718 | 3/2004 | |
| EP | 1741424 | 1/2007 | |
| WO | WO94/02122 | 2/1994 | |
| WO | WO 9505199 A1 * | 2/1995 | |
| WO | WO96/04017 | 2/1996 | |
| WO | WO98/00170 | 1/1998 | |
| WO | WO98/22093 | 5/1998 | |
| WO | WO98/31346 | 7/1998 | |
| WO | WO98/58673 | 12/1998 | |
| WO | WO00/13672 | 3/2000 | |
| WO | WO00/72827 | 12/2000 | |
| WO | WO01/60339 | 8/2001 | |
| WO | WO01/95877 | 12/2001 | |
| WO | WO01/97865 | 12/2001 | |
| WO | WO02/00207 | 1/2002 | |
| WO | WO02/17884 | 3/2002 | |
| WO | WO02/45575 | 6/2002 | |
| WO | WO02/083154 | 10/2002 | |
| WO | WO03/030872 | 4/2003 | |
| WO | WO03/092659 | 11/2003 | |
| WO | WO03/105780 | 12/2003 | |
| WO | WO2004/006897 | 1/2004 | |
| WO | WO2004/012690 | 2/2004 | |
| WO | WO2004/019908 | 3/2004 | |
| WO | WO2004/030659 | 4/2004 | |
| WO | WO2004/041991 | 5/2004 | |
| WO | WO2004/082660 | 9/2004 | |
| WO | WO2004/112695 | 12/2004 | |
| WO | WO2004/112696 | 12/2004 | |
| WO | WO2005/007080 | 1/2005 | |
| WO | WO2005/032511 | 4/2005 | |
| WO | WO2005/055976 | 6/2005 | |
| WO | WO2005/084644 | 9/2005 | |
| WO | WO2005/115330 | 12/2005 | |
| WO | WO2006/002140 | 1/2006 | |
| WO | WO2006/003504 | 1/2006 | |
| WO | WO2006/036617 | 4/2006 | |
| WO | WO 2006090150 A1 * | 8/2006 | A61K 9/146 |
| WO | WO2006/130943 | 12/2006 | |
| WO | WO2007/064912 | 6/2007 | |
| WO | WO2007/146943 | 12/2007 | |
| WO | WO2008/038111 A1 | 4/2008 | |
| WO | WO2008/070538 | 6/2008 | |
| WO | WO2008/092057 | 7/2008 | |
| WO | WO2008/137960 | 11/2008 | |
| WO | WO2008/151022 | 12/2008 | |
| WO | WO2009/046440 | 4/2009 | |
| WO | WO2010/009146 | 1/2010 | |
| WO | WO2010/102066 | 9/2010 | |
| WO | WO2010/132827 | 11/2010 | |
| WO | WO2010/146406 | 12/2010 | |
| WO | WO2010/146408 | 12/2010 | |
| WO | WO2010/146409 | 12/2010 | |
| WO | WO2011/057017 | 5/2011 | |
| WO | WO2011/060250 | 5/2011 | |

OTHER PUBLICATIONS

Heinze et al., "Functional Polymers Based on Dextran," *Advances in Polymer Science*, vol. 205, pp. 199-291 (Sep. 2006).

Hornig, et al., "Nanoscale Structures of Dextran Esters," *Carbohydrate Polymers*, vol. 68, pp. 280-286 (2007).

Kawashima et al., "A New Powder Design Method to Improve Inhalation Efficiency of Pranlukast Hydrate Dry Powder Aerosols by Surface Modification with Hydroxypropylmethylcellulose Phthalate Nanospheres," *Pharmaceutical Research*, vol. 15, No. 11, pp. 1748-1752 (Nov. 1998).

Lemarchand et al., "Influence of polysaccharide coating on the interactions of nanoparticles with biological systems," *Biomaterials*, vol. 27, Issue 1, pp. 108-118 (Jan. 2006).

(56) References Cited

OTHER PUBLICATIONS

Liebert et al., "Nanoparticles on the Basis of Highly Functionalized Dextrans," *Journal of the American Chemical Society*, vol. 127, No. 30, pp. 10484-10485 (Aug. 2005).

Niwa et al., "Aerosolization of Lactide/Glycolide Copolymer (PLGA) Nanospheres for Pulmonary Delivery of Peptide-drugs," *Yakugaku Zasshi Journal of the Pharmaceutical Society of Japan*, vol. 115, No. 9, pp. 732-741 (Sep. 1995).

Prado et al., "Preparation and characterization of a novel starch-based interpolyelectrolyte complex as matrix for controlled drug release," *Carbohydrate Research*, vol. 344, No. 11, pp. 1325-1331 (Jul. 2009).

Rasenack et al., "Micronization of Anti-Inflammatory Drugs for Pulmonary Delivery by a Controlled Crystallization Process," *Journal of Pharmaceutical Sciences*, vol. 92, No. 1, pp. 35-44 (Jan. 2003).

Sham et al., "Formulation and characterization of spray-dried powders containing nanoparticles for aerosol delivery to the lung," *International Journal of Pharmaceutics*, vol. 269, Issue 2, pp. 457-467 (Jan. 2004).

Steckel et al., "In-situ-micronization of disodium cromoglycate for pulmonary delivery," *European Journal of Pharmaceutics and Biopharmaceutics*, vol. 55, No. 2, pp. 173-180 (Mar. 2003).

Steckel et al., "In vitro characterization of jet-milled and in-situ-micronized fluticasone-17-propionate," *International Journal of Pharmaceutics*, vol. 258, Issues 1-2, pp. 65-75 (Jun. 2003).

Yamamoto et al., "Poly(lactic-co-glycolic acid) Nanosphere Composite Prepared with Mechanofusion Dry Powder Composition System for Improving Pulmonary Insulin Delivery with Dry Powder Inhalation," *Journal of Pharmaceutical Science and Technology*, Japan, vol. 64, No. 4, pp. 245-253 (Jan. 2004).

\* cited by examiner

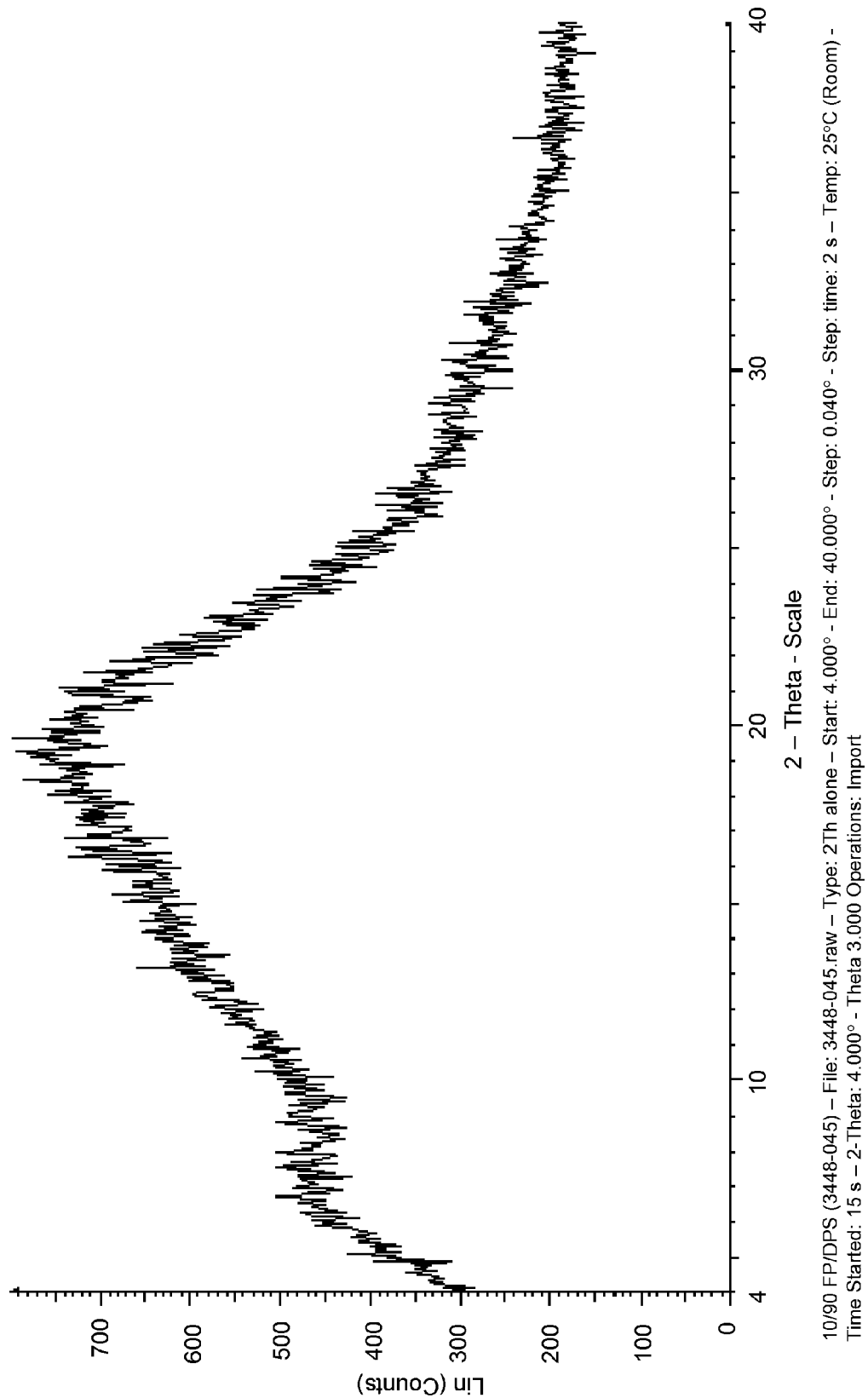

PHARMACEUTICAL COMPOSITIONS OF DEXTRAN POLYMER DERIVATIVES

CROSS REFERENCE TO RELATED APPLICATIONS

This is a continuation of application Ser. No. 13/254,802, filed Sep. 2, 2011, which is the U.S. National Stage of International Application No. PCT/US2010/026127, filed Mar. 3, 2010, which was published in English under PCT Article 21(2), which in turn claims the benefit of U.S. Provisional Patent Application No. 61/157,854, filed Mar. 5, 2009, and U.S. Provisional Patent Application No. 61/178,690, filed May 15, 2009, each of which is incorporated herein in its entirety by reference.

TECHNICAL FIELD

Pharmaceutical compositions are provided comprising an active agent and a dextran polymer derivative.

BACKGROUND

Pharmaceutically active agents are generally formulated as solid or liquid dosage forms for administration. Such dosage forms generally comprise the active agent combined with excipients to form materials that may be conveniently and reliably administered to a patient in need of such therapy, and following administration, the active agent is absorbed and distributed in the patient in a way that leads to good efficacy and safety.

For example, when a low-solubility active agent is dosed orally, it is sometimes desired to form a solid amorphous dispersion of the active agent and a polymer in order to enhance the absorption of the active agent. One reason for forming solid amorphous dispersions is that the aqueous dissolved active agent concentration of a poorly aqueous soluble active agent may be improved by forming an amorphous dispersion of the active agent and a polymer. For example, Curatolo et al., EP 0 901 786 B1 disclose forming pharmaceutical spray-dried dispersions of sparingly soluble drugs and the polymer hydroxypropyl methyl cellulose acetate succinate (HPMCAS). Such solid amorphous dispersions of drug and polymer provide higher concentrations of dissolved drug in an aqueous solution compared with the drug in crystalline form. Such solid amorphous dispersions tend to perform best when the drug is homogeneously dispersed throughout the polymer.

In another example, an active agent is combined with a polymer and formed into nanoparticles, having an effective diameter of less than about 400 nm. Such nanoparticles can be used for a wide variety of delivery routes, including oral, injectable, ocular, and pulmonary delivery of the active agent.

For most non-oral delivery routes, it is desired that the excipients used in the formulation be at least biocompatible, or preferably biodegradable. However, many of the excipients used in oral formulations, and especially polymers, are not biodegradable or biocompatible. Those pharmaceutically acceptable polymers that are biodegradable or biocompatible often do not have the desired or required properties for effectively formulating the active agent into the desired form. For example, most polymers that can be safely used for parenteral delivery are highly water soluble. As a result, they are typically inappropriate for use in making aqueous suspensions of nanoparticles or other types of dosage forms such as long-acting depots.

What is desired is a pharmaceutical composition comprising an active agent and a polymer, wherein the polymer has improved properties that make the composition suitable for a wide range of applications.

SUMMARY

A pharmaceutical composition comprises from 0.01 to 99 wt % of an active agent and from 1 to 99.99 wt % of a dextran polymer derivative. The dextran polymer derivative is selected from dextran acetate, dextran propionate, dextran succinate, dextran acetate propionate, dextran acetate succinate, dextran propionate succinate, dextran acetate propionate succinate, and mixtures thereof. In some embodiments, the dextran polymer derivative is selected from the group consisting of dextran acetate, dextran propionate, dextran succinate, dextran acetate propionate, dextran acetate succinate, dextran propionate succinate, dextran acetate propionate succinate, and mixtures thereof.

In one embodiment, at least 50 wt % of the composition is comprised of the active agent and dextran polymer derivative. In another embodiment, at least 75 wt % of the composition consists essentially of the active agent and the dextran polymer derivative. In yet another embodiment, at least 90 wt % of the composition consists essentially of the active agent and the dextran polymer derivative. In still another embodiment, the composition consists essentially of the active agent and the dextran polymer derivative.

In one embodiment, the composition comprises a plurality of particles comprising the active agent and the dextran polymer derivative. In another embodiment, the composition is in the form of a coating on a substrate.

In one embodiment, the composition is in the form of a solid dispersion of the active agent and the dextran polymer derivative, wherein at least 90 wt % of the active agent in the dispersion is non-crystalline. In another embodiment, at least 90 wt % of the active agent is in the form of a solid solution in the dispersion.

In another embodiment, the composition comprising an active agent and the dextran polymer derivative is in the form of nanoparticles, wherein the nanoparticles have an average size of less than 500 nm.

In still another embodiment, a composition comprises (a) nanoparticles comprising the active agent, wherein the nanoparticles have an average size of less than 500 nm; and (b) a resuspending material comprising the dextran polymer derivative; wherein from 5 wt % to 90 wt % of the combined mass of (1) the nanoparticles and (2) the resuspending material comprises the resuspending material.

In yet another embodiment, the active agent is present in the dextran polymer derivative in a form selected from at least one of crystalline and semi-crystalline active agent having a size of less than 400 nm in at least one dimension.

In one embodiment, the dextran polymer derivative has a total degree of substitution of acetate, propionate, and succinate groups of greater than or equal to 0.05. In another embodiment, the dextran polymer derivative has a total degree of substitution of acetate, propionate, and succinate groups of greater than or equal to 0.25.

In yet another embodiment, the composition consists essentially of the active agent and the dextran polymer derivative.

In yet another embodiment, the dextran polymer derivative is selected from dextran acetate succinate, dextran propionate succinate, dextran acetate propionate succinate, and mixtures thereof. In certain embodiments, the dextran polymer derivative is selected from the group consisting of dextran acetate succinate, dextran propionate succinate, dextran acetate propionate succinate, and mixtures thereof.

In one embodiment, a dosage form comprises a composition comprising from 0.01 to 99 wt % of an active agent and from 1 to 99.99 wt % of a dextran polymer derivative. The dextran polymer derivative is selected from the group consisting of dextran acetate, dextran propionate, dextran succinate, dextran acetate propionate, dextran acetate succinate, dextran propionate succinate, dextran acetate propionate succinate, and mixtures thereof. At least 50 wt % of the composition comprises the active agent and dextran polymer derivative. At least 5 wt % of the dosage form comprises the composition.

In one embodiment, a dosage form comprises a composition comprising an active agent and a dextran polymer derivative, where at least 5 wt % of the dosage form is comprised of the active agent and dextran polymer derivative. In another embodiment, at least 10 wt % of the dosage form consists essentially of the active agent and dextran polymer derivative. In another embodiment, at least 20 wt % of the dosage form consists essentially of the active agent and dextran polymer derivative. In another embodiment, at least 25 wt % of the dosage form consists essentially of the active agent and dextran polymer derivative.

In still another embodiment, the invention provides a method of treating an animal in need of therapy comprising administering an embodiment of the composition to an animal via a mode selected from oral, buccal, mucosal, sublingual, intravenous, intra-arterial, intramuscular, subcutaneous, intraperitoneal, intraarticular, infusion, intrathecal, intraurethral, topical, subdermal, transdermal, intranasal, inhalation, pulmonary tract, intratracheal, intraocular, ocular, intraaural, vaginal, and rectal. In certain embodiments, the composition is administered to an animal via a mode selected from the group consisting of oral, buccal, mucosal, sublingual, intravenous, intra-arterial, intramuscular, subcutaneous, intraperitoneal, intraarticular, infusion, intrathecal, intraurethral, topical, subdermal, transdermal, intranasal, inhalation, pulmonary tract, intratracheal, intraocular, ocular, intraaural, vaginal, and rectal.

The invention provides one or more of the following advantages. The dextran polymer derivatives have a combination of substituent degrees of substitution tailored to provide utility for pharmaceutical compositions.

When used to form combinations of active agents, such polymers provide enhanced concentrations of dissolved active agent in a use environment. When used in combination with active agents that are prone to rapid crystallization from supersaturated aqueous solutions, such polymers are particularly effective at sustaining high concentrations of the active agent and thereby enhancing absorption of active agent in vivo.

When the compositions are dosed parenterally, the compositions of the present invention have the advantage of being at least biocompatible or well tolerated and often have the advantage of being biodegradable.

The foregoing and other objectives, features, and advantages of the invention will be more readily understood upon consideration of the following detailed description of the invention.

BRIEF DESCRIPTION OF THE DRAWINGS

FIG. 1 is a FIGURE showing the results of powder X-ray diffraction of a sample of the dispersion of Example 1.

DETAILED DESCRIPTION

Pharmaceutical compositions are provided comprising an active agent and a dextran polymer derivative. Dextran polymer derivatives, active agents, suitable compositions and methods for making them, and suitable methods for delivering the compositions to a patient in need of therapy are described in detail below.

Unless otherwise indicated, all numbers expressing quantities of ingredients, properties such as molecular weight, percentages, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Dextran Polymer Derivatives

Dextran polymer derivatives are polymers formed by the derivatization of dextran with ester-linked groups. The groups ester-linked to the dextran may be acetate, propionate, succinate, or any combination of the three groups. Dextran is an α-D-1,6-glucose-linked glucan. It may have side-chains linked to the backbone of the dextran polymer, with the degree of branching being approximately 5%, and the branches being mostly 1-2 glucose units long. A fragment of the dextran structure is illustrated below.

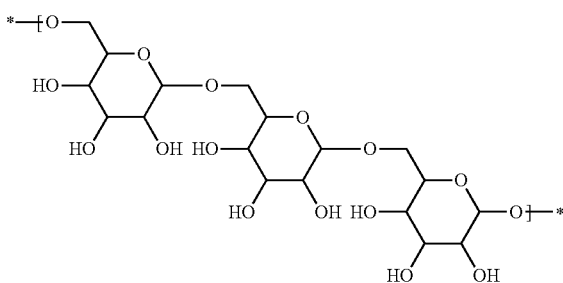

The term "dextran polymer derivative" refers to any of the family of dextran polymers that have acetate, propionate, and/or succinate groups attached via ester linkages to a significant fraction of the dextran polymer's hydroxyl groups.

In one embodiment, the dextran polymer derivative is selected from the group consisting of dextran acetate, dextran propionate, dextran succinate, dextran acetate propionate, dextran acetate succinate, dextran propionate succinate, dextran acetate propionate succinate, and mixtures thereof. In another embodiment, the dextran polymer derivative is dextran acetate succinate. In yet another embodiment, the dextran polymer derivative is dextran propionate succinate.

For example, a fragment of dextran propionate succinate is illustrated below.

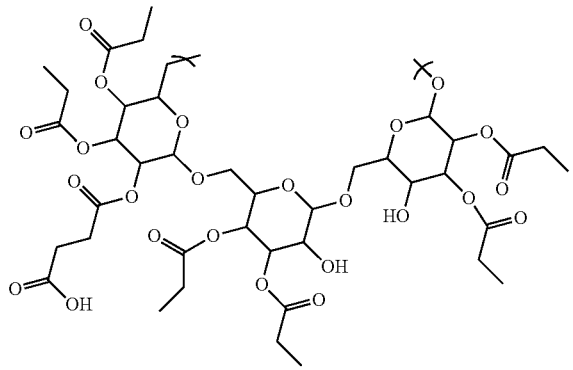

The degree of substitution of each substituent is chosen so that the active agent combined with the dextran polymer derivative will be suitable for the intended formulation. "Degree of substitution" or "DS" refers to the average number of the three hydroxyls per saccharide repeat unit on the dextran chain that have been substituted. For example, if all of the hydroxyls on the dextran chain have been substituted by acetate groups, the degree of substitution of acetate groups is 3. In the structure of dextran propionate succinate shown above, the degree of substitution of propionate groups is 2, while the degree of substitution of succinate groups is 0.33.

In one embodiment, the degree of substitution of the acetate, propionate, and succinate groups are such that when adding the total degree of substitution of acetate, propionate and succinate, the total degree of substitution is greater than or equal to 0.05. In another embodiment, the total degree of substitution is greater than or equal to 0.15. In another embodiment, the total degree of substitution is greater than or equal to 0.25. In still another embodiment, the total degree of substitution is greater than or equal to 0.50. In yet another embodiment, the total degree of substitution is greater than or equal to 0.75.

In one embodiment, the dextran polymer derivative is dextran acetate, wherein the degree of substitution for acetate groups ranges from 0.05 to 3.0. In another embodiment, the dextran polymer derivative is dextran acetate, wherein the degree of substitution for acetate groups ranges from 0.05 to 2.0. In another embodiment, the dextran polymer derivative is dextran acetate, wherein the degree of substitution for acetate groups ranges from 0.25 to 1.8. In another embodiment, the dextran polymer derivative is dextran acetate, wherein the degree of substitution for acetate groups is greater than 1.0.

In still another embodiment, the dextran polymer derivative is dextran propionate, wherein the degree of substitution for propionate groups ranges from 0.05 to 3.0. In another embodiment, the dextran polymer derivative is dextran propionate, wherein the degree of substitution for propionate groups ranges from 0.05 to 2.0. In another embodiment, the dextran polymer derivative is dextran propionate, wherein the degree of substitution for propionate groups ranges from 0.25 to 2.0. In another embodiment, the dextran polymer derivative is dextran propionate, wherein the degree of substitution for propionate groups ranges from 0.5 to 2.0. In another embodiment, the dextran polymer derivative is dextran propionate, wherein the degree of substitution for propionate groups is greater than 1.0.

In still another embodiment, the dextran polymer derivative is dextran succinate, wherein the degree of substitution for succinate groups ranges from 0.05 to 3.0. In another embodiment, the dextran polymer derivative is dextran succinate, wherein the degree of substitution for succinate groups ranges from 0.05 to 2.8. In another embodiment, the dextran polymer derivative is dextran succinate, wherein the degree of substitution for succinate groups ranges from 0.5 to 2.5.

In another embodiment, the dextran polymer derivative is dextran acetate propionate, wherein the degree of substitution for acetate groups ranges from 0.05 to 2.5, and the degree of substitution for propionate groups ranges from 0.05 to 2.5. In another embodiment, the dextran polymer derivative is dextran acetate propionate, wherein the degree of substitution for acetate groups ranges from 0.1 to 2.0, and the degree of substitution for propionate groups ranges from 0.1 to 2.0.

In another embodiment, the dextran polymer derivative is dextran acetate succinate, wherein the degree of substitution for acetate groups ranges from 0.25 to 2.5, and the degree of substitution for succinate groups ranges from 0.05 to 1.5. In another embodiment, the dextran polymer derivative is dextran acetate succinate, wherein the degree of substitution for acetate groups ranges from 0.5 to 2.5, and the degree of substitution for succinate groups ranges from 0.05 to 1.5. In still another embodiment, the dextran polymer derivative is dextran acetate succinate, wherein the degree of substitution for acetate groups ranges from 1.0 to 2.3, and the degree of substitution for succinate groups ranges from 0.1 to 1.5.

In another embodiment, the dextran polymer derivative is dextran propionate succinate, wherein the degree of substitution for propionate groups ranges from 0.1 to 2.5, and the degree of substitution for succinate groups ranges from 0.05 to 1.5. In another embodiment, the dextran polymer derivative is dextran propionate succinate, wherein the degree of substitution for propionate groups ranges from 0.25 to 2.0, and the degree of substitution for succinate groups ranges from 0.1 to 1.5.

In another embodiment, the dextran polymer derivative is dextran acetate propionate succinate, wherein the degree of substitution for acetate groups ranges from 0.05 to 2.5, the degree of substitution for propionate groups ranges from 0.05 to 2.5, and the degree of substitution for succinate groups ranges from 0.05 to 1.5. In another embodiment, the dextran polymer derivative is dextran acetate propionate succinate, wherein the degree of substitution for acetate groups ranges from 0.1 to 2.0, the degree of substitution for propionate groups ranges from 0.1 to 2.0, and the degree of substitution for succinate groups ranges from 0.1 to 1.5.

In one embodiment, the dextran polymer derivative has a degree of substitution of succinate that is 0.05 or more. A degree of substitution of succinate groups of 0.05 or more is desirable as this imparts a negative charge to the polymer at physiologically relevant pH ranges (pH 1-8). When making nanoparticles comprising the active agent and a dextran polymer derivative with a $DS_{succinate} \geq 0.05$, this charge serves to stabilize the nanoparticles, minimizing or avoiding aggregation. For solid dispersions, the succinate groups, combined with the acetate and/or propionate groups, yields stable. Finally, the presence of succinate groups allows the dextran polymer derivative to be relatively hydrophobic in its protonated form for dissolution in organic solvents; for physical stability, resulting in low water absorption; and for compatibility with hydrophobic active agents. In one embodiment, a dextran polymer derivative with a $DS_{succinate} \geq 0.05$ is water soluble or dispersible when ionized, as it is in pH environments above about pH 5 (e.g., in vivo).

In one embodiment, the dextran used to form the dextran polymer derivative has a molecular weight that may range from 1,000 to 200,000 daltons. As used herein, by "molecular weight" is meant the number-average molecular weight as determined by chromatographic methods well known in the art. In these methods, the number-average molecular weight corresponds to the arithmetic mean of the molecular weights of individual macromolecules. In one embodiment, the dextran used to form the dextran polymer derivative has a molecular weight of from 1,000 to 200,000 daltons. In another embodiment, the dextran used to form the dextran polymer derivative has a molecular weight of from 2,000 to 70,000 daltons. In still another embodiment, the dextran used to form the dextran polymer derivative has a molecular weight of from 2,000 to 25,000 daltons.

Thus, in one embodiment, the dextran polymer derivative has a molecular weight of from 1,000 to 200,000 daltons. In another embodiment, the dextran polymer derivative has a molecular weight ranging from 3,000 daltons to 100,000 daltons. In another embodiment, the dextran polymer derivative has a molecular weight of from 3,000 to 70,000 daltons. In still another embodiment, the dextran polymer derivative has a molecular weight of from 2,000 to 25,000 daltons.

The degree of substitution of the substituents may be chosen such that the polymer has the desired physical properties. In one embodiment, the degree of substitution is adjusted to obtain a dextran polymer derivative with the desired aqueous solubility or dispersability. A test to determine the aqueous solubility of a dextran polymer derivative may be performed as follows. The dextran polymer derivative is initially present in bulk powder form with an average particle size of greater than about 1 micron. The polymer alone is administered at a concentration of 0.2 mg/mL to a buffer solution at the desired pH and stirred for approximately 1 hour at room temperature. Next, a nylon 0.45 μm filter is weighed, and the solution is filtered. The filter is then dried overnight at 40° C., and weighed the next day. The aqueous solubility of the polymer is calculated from the amount of polymer added to the buffer solution minus the amount of polymer remaining on the filter.

Similar procedures can be used to determine the effect of pH on the aqueous solubility of the dextran polymer derivatives. In this case the procedures are performed using aqueous buffer solutions with various pH values.

In one embodiment, the dextran polymer derivative is aqueous soluble. By "aqueous soluble" is meant that the dextran polymer derivative has an aqueous solubility of at least 1 mg/mL over at least a portion of the physiologically relevant pH range of 1-8. When the dextran polymer derivative is dextran acetate, the $DS_{acetate}$ should be less than about 1.5. When the dextran polymer derivative is dextran propionate, the $DS_{propionate}$ should be less than about 1.3. When the dextran polymer derivative is dextran acetate propionate, the combined degree of substitution of acetate and propionate should be less than about 1.5, with the combined degree of substitution lower as the percentage of propionate relative to acetate increases. When the dextran polymer derivative also includes a $DS_{succinate}$ of ≥0.05, somewhat higher degrees of substitution of acetate and propionate can be tolerated with the polymer being aqueous soluble. Generally, increasing the degree of substitution of succinate also promotes solubility of the dextran polymer derivative at pH values above about 5.0.

In another embodiment, the degree of substitution on the dextran polymer derivative is chosen so that the dextran polymer derivative is an enteric polymer. By "enteric polymer" is meant that the polymer has an aqueous solubility of less than 0.1 mg/mL at a pH of about 3.0 or less, and an aqueous solubility of at least 1 mg/mL at a pH of greater than about 7. The actual pH above which it is desired for the dextran polymer derivative to become aqueous soluble will depend on the application and can be varied by adjusting the ratio of the acetate plus propionate groups to the succinate groups. The pH value where the polymer becomes soluble will generally increase from about 3 to about 7 as the ratio of acetate plus propionate groups to succinate groups increases.

In still another embodiment, the degree of substitution on the dextran polymer derivative is chosen so that the dextran polymer derivative is poorly aqueous soluble. By "poorly aqueous soluble" is meant that the polymer has a solubility of less than 0.1 mg/mL over at least a portion of the physiologically relevant pH range of 1-8. Generally, for a dextran polymer derivative to be poorly aqueous soluble, the combined degree of substitution of acetate and propionate is high (greater than about 1), while the degree of substitution of succinate is low (less than about 0.1).

The degree of substitution of substituents may also be used to form dextran polymer derivatives with other desirable properties, depending on the formulation desired. For example, in some embodiments, it is desirable that the absorption of water by the polymer be low, such as for powders for pulmonary delivery of the composition. A relatively high degree of substitution of any of the acetate, propionate, or succinate groups or combinations thereof will result in a dextran polymer derivative that absorbs less water from the surrounding atmosphere relative to compositions formed from underivatized dextran. In some embodiments, this leads to increased stability of the active agent in the composition. In particular, when the composition is a powder, low absorption of water can lead to the Tg of the composition being higher and therefore the powder being resistant to agglomeration (e.g., for respirable particles) and, when the composition is a solid dispersion, the active agent will tend to remain dispersed and not separate from the polymer as amorphous or crystalline active agent domains.

Thus, in one embodiment, the degree of substitution of acetate, propionate, and succinate are chosen such that the mass of water absorbed by the dextran polymer derivative is significantly less than that absorbed by underivatized dextran. In one embodiment, the mass of water absorbed by the dextran polymer derivative is at least 10% less than that absorbed by underivatized dextran when measured by dynamic vapor absorption at 90% relative humidity (RH) and 25° C. For comparison, the mass of water absorbed by underivatized dextran, when measured by dynamic vapor absorption at 90% RH and 25° C. is about 26 wt %. Thus, in one embodiment, the dextran polymer derivative absorbs less than 23 wt % water when measured by dynamic vapor absorption at 90% RH at 25° C. In another embodiment, the dextran polymer derivative absorbs less than 20 wt % water at 90% RH at 25° C. In still another embodiment, the dextran polymer derivative absorbs less than 18 wt % water at 90% RH at 25° C.

The addition of ester-linked acetate, propionate, and succinate groups to the dextran polymer to reduce water absorption also results in the glass-transition temperature (Tg) of the polymer equilibrated with a humid atmosphere being higher than that of the corresponding underivatized dextran. This higher Tg is desirable for some compositions comprising an active agent and dextran polymer derivative, for example, for long-term stability of compositions comprising non-crystalline active agent.

Thus, in one embodiment, the degree of substitution of acetate, propionate, and succinate is chosen such that the Tg of the dextran polymer derivative is significantly higher than that of underivatized dextran when exposed to a humid atmosphere. In one embodiment, the Tg of the dextran polymer derivative is at least 10° C. greater than that of underivatized dextran when the powders are exposed to a 50% RH atmosphere at 25° C. For comparison, the Tg of underivatized dextran powder when exposed to a 50% RH atmosphere at 25° C. is about 45 to 50° C. Thus, in one embodiment, the Tg of the dextran polymer derivative is at least 50° C. when exposed to a 50% RH atmosphere at 25° C. In another embodiment, Tg of the dextran polymer derivative is at least 60° C. when exposed to a 50% RH atmosphere at 25° C.

In one embodiment, the dextran polymer derivative is biocompatible. By "biocompatible" is meant that for some delivery routes, the polymer is compatible with and has no significant toxic effect on the living organism to which it is administered. In one embodiment, the polymer does not significantly elicit humoral or cell-based immune responses when administered in vivo.

In yet another embodiment, the dextran polymer derivative is biodegradable. By "biodegradable" is meant that the polymer will degrade when administered in vivo. By "degrade" is meant that in an in vivo use environment, the polymer is broken down into smaller species that can be absorbed, metabolized, or otherwise eliminated or "cleared" from the use environment. This degradation can occur through enzymatic, hydrolytic, oxidative, or other reaction, as is well known in the art. The polymer may also degrade into aqueous soluble species that can be cleared from the in vivo use environment. For example, the degradation products may be renally cleared through the kidneys or may enter the lymphatic system and then exit through the gastro-intestinal tract.

Synthesis of Dextran Polymer Derivatives

Methods for preparation of ester derivatives of carbohydrates are known. See for example Advances in Polymer Science, 205, *Polysaccharides II*, Edited by Dieter Klemm (Springer-Verlag, Berlin Heidelberg, 2006). Methods for the preparation of the dextran polymer derivatives of the present invention can be derived from such known methods. Specifically, the dextran polymer derivatives can be prepared as follows. In a first method, dextran is first modified by substitution with an alkyl group followed by addition of succinate. The dextran is first dissolved in a suitable solvent system such as formamide, dimethyl formamide (DMF), or N-methylpyrrolidone (NMP), together with a base, such as pyridine or the sodium salt of the carboxylate corresponding to the alkyl group to be substituted. An anhydride of the alkyl group to be substituted onto the dextran backbone is then added to the mixture. The reaction mixture is then stirred at temperatures ranging from 0 to 100° C. for a period of from about 30 minutes to 72 hours. When the resulting dextran polymer derivative is poorly aqueous soluble, the reaction can then be quenched by adding water to precipitate the polymer. The resulting precipitate can be collected by filtration. Alternatively, the polymer can be isolated by extraction into a solvent, such as ethyl acetate or methylene chloride, and the extraction solvent removed, for example, by evaporation or spray drying. The polymer can be further rinsed, filtered and dried prior to use.

The resulting dextran polymer derivative is then dissolved in the carboxylic acid corresponding to the alkyl group that has been substituted together with the sodium salt of the corresponding carboxylate. For example, if dextran propionate has been prepared, then it is dissolved in propionic acid together with sodium propionate. Succinic anhydride is then added. The reaction mixture may then be stirred at temperatures ranging from 0 to 100° C. for a period of from about 30 minutes to 72 hours. The reaction may then be quenched by adding water to precipitate the polymer. The resulting precipitate may be collected by filtration. Alternatively, the polymer may be isolated by extraction into a solvent, such as ethyl acetate or methylene chloride, and the extraction solvent removed, for example, by evaporation or spray drying. The polymer may be further rinsed, filtered and dried prior to use.

In another method, dextran is first modified by substitution with an alkyl group followed by addition of succinate, but the dextran alkyl ester is not isolated and purified prior to addition of the succinic anhydride. In this method, the dextran alkyl ester is first formed, followed by addition of succinic anhydride.

In yet another method, the dextran is modified by substitution with an alkyl group and succinate simultaneously. In this method, dextran may be first dissolved in a suitable solvent system such as formamide, DMF, or NMP, together with the sodium salt of the carboxylate corresponding to the alkyl group to be substituted. An anhydride of the alkyl group to be substituted onto the dextran backbone and succinic anhydride may then be added to the mixture. The reaction mixture may then be stirred at temperatures ranging from 0 to 100° C. for a period of from about 30 minutes to 72 hours. The reaction may then be quenched by adding water to precipitate the polymer. The resulting precipitate may be collected by filtration. Alternatively, the polymer may be isolated by extraction into a solvent, such as ethyl acetate or methylene chloride, and the extraction solvent removed, for example, by evaporation or spray drying. The polymer may be further rinsed, filtered and dried prior to use.

The degree of substitution of alkyl esters and succinate groups on the dextran polymer may be determined using standard techniques, such as nuclear magnetic resonance (NMR) analysis or high-performance liquid chromatography (HPLC). For example, $^{13}$C NMR analysis may be used to determine the number of alkyl ester and succinate groups using the ratio of the peak area of the groups to the peak area of the anomeric carbon in the dextran ring.

Active Agents

Compositions containing dextran polymer derivatives are suitable for use with any biologically active compound desired to be administered to a patient in need of the active agent. The compositions may contain one or more active agents. As used herein, by "active agent" is meant a drug, medicament, pharmaceutical, therapeutic agent, nutraceutical, or other compound that may be desired to be administered to the body. The active agent may be a "small molecule," generally having a molecular weight of about 2000 Daltons or less. The active agent may also be a "biological active agent." Biological active agents include proteins, antibodies, antibody fragments, peptides, oligoneucleotides, vaccines, and various derivatives of such materials. In one embodiment, the active agent is a small molecule. In another embodiment, the active agent is a biological active agent. In still another embodiment, the active agent is a mixture of a small molecule and a biological active agent.

The active agent may be highly water soluble (i.e., greater than 100 mg/mL), sparingly water soluble (i.e., 5-30 mg/mL), or poorly water soluble (i.e., less than 5 mg/mL). In one embodiment, the active agent is "poorly water soluble," and the active agent has a solubility in water (over the pH range of 6.5 to 7.5 at 25° C.) of less than 5 mg/mL. The active agent may have an even lower aqueous solubility, such as less than about 1 mg/mL, less than about 0.1 mg/mL, and even less than about 0.01 mg/mL.

The active agent should be understood to include the nonionized form of the active agent, pharmaceutically acceptable salts of the active agent, or any other pharmaceutically acceptable forms of the active agent. By "pharmaceutically acceptable forms" is meant any pharmaceutically acceptable derivative or variation, including stereoisomers, stereoisomer mixtures, enantiomers, solvates, hydrates, isomorphs, polymorphs, pseudomorphs, neutral forms, salt forms and prodrugs.

Examples of classes of active agents include, but are not limited to, compounds for use in the following therapeutic areas: antihypertensives, antianxiety agents, antiarrythmia agents, anticlotting agents, anticonvulsants, blood glucose-lowering agents, decongestants, antihistamines, antitussives, antineoplastics, beta blockers, anti-inflammatories, antipsychotic agents, cognitive enhancers, anti-atherosclerotic agents, cholesterol-reducing agents, triglyceride-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-angiogenesis agents, anti-glaucoma agents, anti-depressants, bronchodilators, glucocorticoids, steroids, and antiviral agents.

Compositions Comprising Active Agent and Dextran Polymer Derivatives

The compositions of the present invention comprise an active agent and a dextran polymer derivative. In one embodiment, the compositions are in the form of a plurality of particles. In one embodiment, each of the particles comprises the active agent and the dextran polymer derivative. As used herein, the term "particles" means a small piece of matter having a characteristic diameter of less than about 3000 μm. In another embodiment, the particles are granulated into granules using standard methods known in the art, such as dry granulation, wet granulation, high shear granulation, and the like.

In another embodiment, the composition is in the form of a layer or coating on a substrate. The coating may be formed by spray coating, powder coating, press coating, and other methods known in the art. In this embodiment, the composition is distinct from and separate from the substrate onto which the composition is coated.

In one embodiment, the active agent and dextran polymer derivative constitute at least 50 wt % of the composition. In another embodiment, the active agent and dextran polymer derivative constitute at least 75 wt % of the composition. In still another embodiment, the active agent and dextran polymer derivative constitute at least 90 wt % of the composition. In yet another embodiment, the composition consists essentially of the active agent and the dextran polymer derivative.

In one embodiment, compositions are in the form selected from the group consisting of (1) a solid dispersions, (2) nanoparticles, (3) microparticles (i.e., particles having a characteristic diameter of greater than about 400 nm), (4) solid materials for reconstitution as suspensions, and (5) solid materials where multiple small crystalline or semi-crystalline or amorphous active agent domains are dispersed in larger particles or solid objects comprising the dextran polymer derivative. These embodiments are discussed herein below.

Solid Dispersions

In one embodiment, the composition is in the form of a solid dispersion comprising the active agent and the dextran polymer derivative, wherein at least 90 wt % of the active agent in the dispersion is non-crystalline. In one embodiment, the dextran polymer derivative may be aqueous soluble, enteric, or poorly aqueous soluble. In another embodiment, the dextran polymer derivative is aqueous soluble or enteric.

The relative amounts of active agent and dextran polymer derivative in the dispersion may range from 0.01 wt % to 99 wt % active agent, and from 1 wt % to 99.99 wt % dextran polymer derivative. In other embodiments, the amount of active agent may range from 0.1 wt % to 80 wt %, or from 0.1 to 60 wt %, or from 1 to 40 wt %. The amount of dextran polymer derivative may range from 20 wt % to 99.9 wt %, 40 wt % to 99.9 wt % or from 60 wt % to 99 wt %. In still another embodiment, the dispersions have the following composition: from 0.1 to 80 wt % active agent, and from 20 to 99.9 wt % dextran polymer derivative. In yet another embodiment, the dispersions have the following composition: from 0.1 to 60 wt % active agent, and from 40 to 99.9 wt % dextran polymer derivative. In another embodiment, the dispersions have the following composition: from 1 to 40 wt % active agent, and from 60 to 99 wt % dextran polymer derivative.

In one embodiment, at least 90 wt % of the active agent present in the dispersion is amorphous. By "amorphous" is meant that the active agent is non-crystalline as determined by differential scanning calorimetry, powder X-ray diffraction (PXRD), by solid state nuclear magnetic resonance (NMR), or by any other known quantitative measurement.

As the dextran polymer derivative is amorphous, the dispersion may comprise one or more active agent-rich domains dispersed in a dextran polymer derivative phase, or the dispersion may comprise a "solid solution" of active agent molecules dispersed in the dextran polymer derivative, or the dispersions may comprise any state or combination of states in between. The term "solid solution" includes both thermodynamically stable solid solutions in which the active agent is completely dissolved in the polymer, as well as homogeneous materials consisting of amorphous active agent molecularly dispersed throughout the polymer in amounts greater than the solubility of the active agent in the polymer. A dispersion is considered a "solid solution" when it displays a single Tg when analyzed by differential scanning calorimetry. In one embodiment, the dispersions have at least one Tg due to the amorphous character of the polymer. In another embodiment, essentially all of the active agent and the dextran polymer derivative in the dispersion are in the form of a solid solution. Thus, in one embodiment, the composition consists essentially of a solid solution of the active agent and the dextran polymer derivative.

In another embodiment, the dispersion comprises two or more active agents.

In still another embodiment, the relative amounts of active agent and polymer are chosen so that the dispersions have a glass transition temperature of at least 50° C. at 50% relative humidity. In another embodiment, when evaluated at a relative humidity of less than 5%, the dispersions have a glass transition temperature of at least 50° C., or even at least 80° C., or even at least 100° C. The solid dispersion has a single glass transition temperature, indicating that the solid dispersion is a homogeneous solid solution.

The solid dispersions of the present invention may be formed by any method known in the art, including milling, extrusion, precipitation, or solvent addition followed by solvent removal. For example, active agent and the dextran polymer derivative may be processed by heat, mechanical mixing and extrusion using, for example, a twin-screw extruder. The product may then be milled to the desired particle size. In another example, the active agent and dextran polymer derivative are dissolved in a solvent in which both materials are soluble. The dispersions may then be formed from the solution by any known process, including precipitation in a miscible non-solvent, emulsifying in an immiscible non-solvent, or by forming droplets followed by removal of the solvent by evaporation.

In one embodiment, the solid dispersion is formed by spray drying. The active agent, the dextran polymer derivative, and optional excipients may be dissolved in a solvent. Thus, the fluid that is spray dried may be a suspension or a homogeneous solution or a combination of dissolved and suspended materials. In one embodiment, the fluid that is spray dried comprises a homogeneous solution of active agent and dextran polymer derivative dissolved together in a solvent. In another embodiment, the fluid that is spray dried consists essentially of a solution of active agent and dextran polymer derivative dissolved in a solvent. In still another embodiment, the fluid that is spray dried comprises a suspension of active agent particles in a solution of dextran polymer derivative dissolved in a solvent.

The solvent may be any solvent or mixture of solvents capable of dissolving both the active agent and polymer having a boiling point of less than about 150° C. Suitable solvents include water, acetone, methanol, ethanol, methyl acetate, ethyl acetate, tetrahydrofuran (THF), dichloromethane and mixtures of solvents. When the spray drying solution comprises an organic solvent that is water miscible, such as acetone or methanol, water may be added to the solution. The spray drying solution is then sprayed through an atomizer such as a pressure nozzle or two fluid nozzle into a spray drying chamber. The droplets are contacted with a heated drying gas such as dry nitrogen. Droplets dry rapidly, forming particles of the solid amorphous dispersion comprising the active agent and dextran polymer derivative. The particles exit the spray dryer and are collected, such as in a cyclone.

In one embodiment, the solid dispersion is formed in the presence of a high surface area substrate. Exemplary high surface area substrates include inorganic oxides, such as $SiO_2$ (fumed silica), $TiO_2$, $ZnO_2$, $ZnO$, $Al_2O_3$, zeolites, and inorganic molecular sieves; water insoluble polymers, such as cross-linked cellulose acetate phthalate, cross-linked hydroxypropyl methyl cellulose acetate succinate, cross-linked polyvinyl pyrrolidinone, (also known as cross povidone), cross-linked cellulose acetate phthalate, microcrystalline cellulose, polyethylene/polyvinyl alcohol copolymer, polyethylene polyvinyl pyrrolidone copolymer, cross-linked carboxymethyl cellulose, sodium starch glycolate, cross-linked polystyrene divinyl benzene; and activated carbons. In one embodiment, the substrate is fumed silica. In this embodiment, the solid dispersion may be adsorbed onto the surface of the substrate, coated on the outside of the substrate, or any combination of these.

In another embodiment, the solid dispersion may be formed as a coating on an appropriate substrate. For example, the solid dispersion may be coated onto multiparticulates having diameters ranging from 50 μm to 5,000 μm. In another example, the solid dispersion may be coated onto a tablet or capsule. In still another embodiment, the solid dispersion may be formed into a layer that is incorporated into a tablet.

Nanoparticles

In one embodiment, the composition is in the form of nanoparticles comprising the active agent and the dextran polymer derivative. By "nanoparticles" is meant a plurality of small particles in which the average size of the particles is less than about 500 nm. In suspension, by "average size" is meant the effective cumulant diameter as measured by dynamic light scattering (DLS), using for example, Brookhaven Instruments' 90Plus particle sizing instrument. By "size" is meant the diameter if the particles were spherical particles, or the maximum diameter for non-spherical particles. In some embodiments, the average size of the nanoparticles is less than 400 nm, less 300 nm, less than 200 nm, and even less than 150 nm. In one embodiment, the average size of the nanoparticles is less than 150 nm. In another embodiment, the average size of the nanoparticles is less than 100 nm. In still another embodiment, the average size of the nanoparticles is less than 75 nm. In yet another embodiment, the average size of the nanoparticles is less than 50 nm. In another embodiment, the nanoparticles range in size from 1 nm to 400 nm, from 1 nm to 300 nm, from 1 nm to 200 nm, from 10 nm to 400 nm, or from 30 nm to 400 nm.

The width of the particle size distribution in suspension is given by the "polydispersity" of the particles, which is defined as the relative variance in the correlation decay rate distribution, as is known by one skilled in the art. See B. J. Fisken, "Revisiting the method of cumulants for the analysis of dynamic light-scattering data," Applied Optics, 40(24), 4087-4091 (2001) for a discussion of cumulant diameter and polydispersity. In one embodiment, the polydispersity of the nanoparticles is less than 0.5. In another embodiment, the polydispersity of the nanoparticles is less than about 0.3. In one embodiment, the average size of the nanoparticles is less than 500 nm with a polydispersity of 0.5 or less. In another embodiment, the average size of the nanoparticles is less than 300 nm with a polydispersity of 0.5 or less. In still another embodiment, the average size of the nanoparticles is less than 200 nm with a polydispersity of 0.5 or less. In yet another embodiment, the average size of the nanoparticles is less than 200 nm with a polydispersity of 0.3 or less.

When the composition is in the form of a nanoparticle, the nanoparticles comprising active agent and the dextran polymer derivative, along with other optional excipients that the nanoparticles may be suspended in an aqueous solution without substantially dissolving. In one embodiment, an aqueous solution may be added to a dried form of the nanoparticles to form a concentration suspension for delivery to a use environment such as by injection, subcutaneously or intravascularly. In such cases, the nanoparticles may dissolve upon dilution into the use environment, or alternatively, they may be sufficiently insoluble to remain undissolved for many days. In one embodiment, the dextran polymer derivative may be enteric or poorly aqueous soluble. Thus, in one embodiment, the dextran polymer derivative is enteric. In another embodiment, the dextran polymer derivative is poorly aqueous soluble.

The nanoparticles can exist in a number of different configurations. In one embodiment, the nanoparticles comprise a core, the core comprising the active agent and the dextran polymer derivative. As used herein, the term "core" refers to the interior portion of the nanoparticle. The nanoparticles also have a "surface portion," meaning the outside or exterior portion of the nanoparticle. Thus, the nanoparticles consist of a core (i.e., the interior portion) and a surface portion. In some embodiments, described herein below, materials may be adsorbed to the surface portion of the nanoparticle. Materials adsorbed to the surface portion of the nanoparticle are considered part of the nanoparticle, but are distinguishable from the core of the nanoparticle. Methods to distinguish materials present in the core versus materials adsorbed to the surface portion of the nanoparticle include (1) thermal methods, such as differential scanning calorimetry (DSC); (2) spectroscopic methods, such as X-ray photoelectron spectroscopy (XPS), transmission electron microscopy (TEM) with energy dispersive X-ray (EDX) analysis, Fourier transform infra red (FTIR) analysis, and Raman spectroscopy; (3) chromatographic techniques, such as high performance liquid chromatography (HPLC), and gel-permeation chromatography (GPC); and (4) other techniques known in the art.

The active agent present in the core can exist in pure active agent domains (crystalline or non-crystalline), as a thermodynamically stable solid solution of non-crystalline active agent distributed throughout the dextran polymer derivative, as a supersaturated solid solution of non-crystalline active agent distributed throughout the dextran polymer derivative, or any combination of these states or those states that lie between them. When the glass-transition temperature (Tg) of the non-crystalline active agent is different from the Tg of the pure polymer by at least about 20° C., the core may exhibit a Tg that is different from the Tg of pure non-crystalline active agent or pure polymer. In one embodiment, less than 20 wt % of the active agent is present in non-crystalline active agent domains, with the remaining active agent distributed throughout the polymer.

In one embodiment, the nanoparticles are homogeneous, meaning that the composition on the surface of the nanoparticle is essentially the same as in the core of the nanoparticle. In such cases, the nanoparticles may comprise, in one embodiment, a solid amorphous dispersion of the type described in the previous section, except for the small size—less than 400 nm. In another embodiment, the active agent is present as one or more amorphous or crystalline domains throughout each nanoparticle.

In still another embodiment, the core comprises the active agent and the dextran polymer derivative, with a surface stabilizer adsorbed to the surface portion of the nanoparticle.

In one embodiment, at least 50 wt % of the active agent in the nanoparticles is crystalline. In another embodiment, at least 75 wt % of the active agent in the nanoparticles is crystalline.

In still another embodiment, at least 90 wt % of the active agent in the nanoparticles is non-crystalline. In another embodiment, at least about 95 wt % of the active agent in the nanoparticle is non-crystalline; in other words, the amount of active agent in crystalline form does not exceed about 5 wt %.

Amounts of crystalline active agent may be measured by Powder X-Ray Diffraction (PXRD), by Differential Scanning calorimetry (DSC), by solid state nuclear magnetic resonance (NMR), or by any other known quantitative measurement.

The active agent and polymer are collectively present in the nanoparticle in an amount ranging from about 50 wt % to 100 wt %. In one embodiment, the active agent and polymer collectively may constitute at least 60 wt %, or even at least 80 wt % of the nanoparticle. In another embodiment, the nanoparticles consist essentially of the active agent and the dextran polymer derivative. By "consist essentially of" is meant that the nanoparticle contains less than 1 wt % of any other excipients and that any such excipients have substantially no effect on the performance or properties of the nanoparticle.

The amount of active agent in the nanoparticle may range from 0.01 wt % to 99 wt %. In one embodiment, the amount of active agent in the nanoparticle ranges from 0.1 wt % to 80 wt %, or from 0.1 to 60 wt %, or from 1 to 40 wt %. In still another embodiment, the amount of active agent in the nanoparticle ranges from about 5 wt % to about 75 wt %, from about 5 wt % to about 60 wt %, or from about 5 wt % to about 50 wt %.

To minimize the total mass of the formulation, high active agent loadings are desired. However, if the amount of active agent in the nanoparticle is too high, the nanoparticles suspension becomes unstable, resulting in crystallization of the active agent in the suspension. Additionally, high amounts of active agent in the nanoparticle can lead to crystalline active agent formation when the nanoparticles are isolated from suspension in solid form. Thus, in one embodiment, the amount of active agent in the nanoparticle may be less than about 90 wt %, less than about 80 wt %, or even less than about 75 wt % the total mass of the nanoparticle.

The amount of dextran polymer derivative may range from 1 wt % to 99.99 wt %. The physical stability of the active agent in the nanoparticle tends to improve with increasing amounts of the dextran polymer derivative. Accordingly, in one embodiment, the amount of polymer in the nanoparticle is at least 5 wt %, at least 15 wt %, at least 20 wt %, or at least 25 wt %. However, too much polymer will lead to low active agent loading in the nanoparticle. Thus, in one embodiment, the amount of polymer in the nanoparticle is 80% or less.

The mass ratio of active agent to dextran polymer derivative in the nanoparticle can range from about 1:999 to about 9:1 (that is, from about 0.1 wt % active agent to 90 wt % active agent relative to the total mass of active agent and dextran polymer derivative in the nanoparticle). In one embodiment, the mass ratio of active agent to dextran polymer derivative ranges from about 1:99 to about 4:1 (that is, from about 1 wt % to about 80 wt % active agent relative to the total mass of active agent and dextran polymer derivative), from about 1:19 to about 3:1 (that is, from about 5 wt % to about 75 wt %), from about 1:10 to about 1:5 (that is, from about 9 wt % to about 60 wt % active agent relative to the total mass of active agent and dextran polymer derivative in the nanoparticle). In one embodiment, the mass ratio of active agent to dextran polymer derivative is less than 9:1, less than 4:1, less than 3:1, or even less than 3:2. In other embodiments, the mass ratio of active agent to dextran polymer derivative is at least 1:999, at least 1:99, and even at least 1:10.

The nanoparticles may optionally comprise a surface stabilizer in addition to the active agent and the dextran polymer derivative. The purpose of the surface stabilizer is to reduce or prevent aggregation or flocculation of the nanoparticles in an aqueous suspension, resulting in nanoparticles with improved stability. In one embodiment, the surface stabilizer is used to stabilize the nanoparticles during the formation process. The stabilizer should be inert, in the sense that it does not chemically react with the active agent in an adverse manner, and should be pharmaceutically acceptable.

The surface stabilizer may be distributed throughout the nanoparticle, it may be in higher concentration on the surface of the nanoparticle, or any combination of these. In one embodiment, the surface stabilizer is distributed throughout the nanoparticle. In another embodiment, the surface stabilizer is at a higher concentration on the surface of the nanoparticle. When the surface stabilizer is at a higher concentration on the surface of the nanoparticle, the surface stabilizer may comprise the outer portion of the nanoparticle, while the dextran polymer derivative may be present in the core of the nanoparticle.

When an optional surface stabilizer is present, it may constitute from 0.1 wt % to about 50 wt % of the total mass of the nanoparticles. Generally, lower concentrations of surface stabilizer are desired. Thus, in one embodiment, the surface stabilizer constitutes about 40 wt % or less, or even about 30 wt % or less of the total mass of the nanoparticles.

In one embodiment, the surface stabilizer is an amphiphilic compound, meaning that it has both hydrophobic and hydrophilic regions. In another embodiment, the surface stabilizer is a surfactant, including anionic, cationic, zwitterionic, and non-ionic surfactants. Mixtures of surface stabilizers may also be used.

In one embodiment, the surface stabilizer is a dextran polymer derivative. When the surface stabilizer is a dextran polymer derivative, it may be the same or different than the dextran polymer derivative present in the core of the nanoparticle. In one embodiment, an aqueous soluble dextran polymer derivative is used as the surface stabilizer.

Exemplary surface stabilizers include dextran polymer derivatives, casein, caseinates, dextran, polyvinyl pyrrolidone (PVP), polyoxyethylene alkyl ethers, polyoxyethylene stearates, polyoxyethylene castor oil derivatives, poly(ethylene oxide-propylene oxide) (also known as poloxamers), tragacanth, gelatin, polyethylene glycol, bile salts (such as salts of dihydroxy cholic acids, including sodium and potassium salts of cholic acid, glycocholic acid, and taurocholic acid), phospholipids (such as phosphatidyl cholines, including 1,2-diacylphosphatidylcholine also referred to as PPC or lecithin), sodium dodecylsulfate (also known as sodium lauryl sulfate), benzalkonium chloride, sorbitan esters, polyoxyethylene alkyl ethers, polyoxyethylene castor oil derivatives, polyoxyethylene sorbitan fatty acid esters (polysorbates), polyoxyethylene stearates, triethanolamine, sodium docusate, sodium stearyl fumarate, sodium cyclamate, and mixtures and pharmaceutically acceptable forms thereof.

In one embodiment, the surface stabilizer is a bile salt. The bile salt may be selected from the group sodium glycocholate and sodium taurocholate.

The nanoparticles may be formed by any process that results in formation of nanoparticles comprising active agent and a dextran polymer derivative. The active agent used to form the nanoparticles may be in a crystalline or non-crystalline form, or a mixture thereof.

One process for forming nanoparticles is an emulsification process. In this process, the active agent and dextran polymer derivative are dissolved in an organic solvent that is immiscible with an aqueous solution in which active agent and polymers are poorly soluble, forming an organic solution. Solvents suitable for forming the solution of dissolved active agent and dextran polymer derivative can be any compound or mixture of compounds in which the active agent and the polymer are mutually soluble and which is immiscible with the aqueous solution. As used herein, the term "immiscible" means that the organic solvent has a solubility in the aqueous solution of less than about 10 wt %, less than about 5 wt %, or even less than about 3 wt %. In one embodiment, the solvent is also volatile with a boiling point of 150° C. or less. Exemplary organic solvents include methylene chloride, trichloroethylene, trichloro-trifluoro-ethylene, tetrachloroethane, trichloroethane, dichloroethane, dibromoethane, ethyl acetate, phenol, chloroform, toluene, xylene, ethyl-benzene, benzyl alcohol, creosol, methylethyl ketone, methyl-isobutyl ketone, hexane, heptane, ether, and mixtures thereof. In one embodiment, the organic solvents are methylene chloride, ethyl acetate, benzyl alcohol, and mixtures thereof.

In one embodiment, the aqueous solution is water. The optional surface stabilizer or other components that make up the exterior portion of the nanoparticles may be dissolved in the aqueous solution. When the active is water soluble, it may be dissolved in the aqueous solution.

Once the organic solution is formed, it is then mixed with the aqueous solution and homogenized to form an emulsion of fine droplets of the water immiscible solvent distributed throughout the aqueous phase. The volume ratio of organic solution to aqueous solution used in the process will generally range from 1:100 (organic solution:aqueous solution) to 2:3 (organic solution:aqueous solution). In one embodiment, the organic solution:aqueous solution volume ratio ranges from 1:9 to 1:2 (organic solution:aqueous solution). The emulsion is generally formed by a two-step homogenization procedure. The solution of active agent, polymer and organic solvent are first mixed with the aqueous solution using a rotor/stator or similar mixer to create a "pre-emulsion". This mixture is then further processed with a high-pressure homogenizer that subjects the droplets to very high shear, creating a uniform emulsion of very small droplets. A portion of the organic solvent is then removed forming a suspension of the nanoparticles in the aqueous solution. Exemplary processes for removing the organic solvent include evaporation, extraction, diafiltration, pervaporation, vapor permeation, distillation, and filtration. In one embodiment, the organic solvent is removed to a level that is acceptable according to The International Committee on Harmonization (ICH) guidelines. In another embodiment, the concentration of organic solvent in the nanoparticle suspension is less than the solubility of the organic solvent in the aqueous solution. Even lower concentrations of organic solvent are often desired. Thus, the concentration of organic solvent in the nanoparticle suspension may be less than about 5 wt %, less than about 3 wt %, less than 1 wt %, and even less than 0.1 wt %.

An alternative process to form the nanoparticles is a precipitation process. In this process, the dextran polymer derivative is first dissolved in an organic solvent that is miscible with an aqueous solution in which the dextran polymer derivative is poorly soluble. The resulting organic solution is mixed with the aqueous solution causing the nanoparticles to precipitate. In one embodiment, the active agent is dissolved in the aqueous solution. In another embodiment, the active agent is dissolved, along with the dextran polymer derivative, in the organic solution. Solvents suitable for forming the solution of dissolved active agent and polymer can be any compound or mixture of compounds in which the active agent and the polymer are mutually soluble and which is miscible in the aqueous solution. In one embodiment, the organic solvent is also volatile with a boiling point of 150° C. or less. Exemplary solvents include acetone, methanol, ethanol, tetrahydrofuran (THF), and DMSO. Mixtures of solvents, such as 50% methanol and 50% acetone, can also be used, so long as the active agent and polymer are sufficiently soluble to dissolve the active agent and polymer. In one embodiment, the solvents are methanol, acetone, and mixtures thereof.

The aqueous solution may be any compound or mixture of compounds in which the active agent and polymer are sufficiently insoluble so as to precipitate to form nanoparticles. In one embodiment, the aqueous solution is water. In another embodiment, the optional surface stabilizer is dissolved in the aqueous solution.

The organic solution and aqueous solution are combined under conditions that cause solids to precipitate as nanoparticles. The mixing can be by addition of a bolus or stream of organic solution to a stirring container of the aqueous solution. Alternately a stream or jet of organic solution can be mixed with a moving stream of aqueous solution. In either case, the precipitation results in the formation of a suspension of nanoparticles in the aqueous solution.

For the precipitation process, the amount of active agent and polymer in the organic solution depends on the solubility of each in the organic solvent and the desired ratio of active agent to polymer in the resulting nanoparticles. The organic solution may comprise from about 0.1 wt % to about 20 wt % dissolved solids. A dissolved solids content of from about 0.5 wt % to 10 wt % is usually desired.

The organic solution:aqueous solution volume ratio should be selected such that there is sufficient aqueous solution in the nanoparticle suspension that the nanoparticles solidify and do not rapidly agglomerate. However, too much aqueous solution will result in a very dilute suspension of nanoparticles, which may require further processing for ultimate use. Generally, the organic solution:aqueous solution volume ratio should be at least 1:100, but generally should be less than 1:2 (organic solution:aqueous solution). In one embodiment, the organic solution:aqueous solution volume ratio ranges from about 1:20 to about 1:3.

Once the nanoparticle suspension is made, a portion of the organic solvent may be removed from the suspension using methods known in the art. Exemplary processes for removing the organic solvent include evaporation, extraction, diafiltration, pervaporation, vapor permeation, distillation, and filtration. In one embodiment, the solvent is removed to a level that is acceptable according to ICH guidelines. Thus, the concentration of solvent in the nanoparticle suspension may be less than about 10 wt %, less than about 5 wt %, less than about 3 wt %, less than 1 wt %, and even less than 0.1 wt %.

Still another process for forming nanoparticles is through a milling process, as is known in the art. One method comprises suspending the crystalline active agent in a liquid dispersion medium and applying mechanical means in the presence of grinding media to reduce the particle size of the active agent substance to the effective average particle size. The particles can be reduced in size in the presence of a dextran polymer derivative, which acts as a surface modifier. Alternatively, the particles can be contacted with the dextran polymer derivative after attrition.

Resuspending Materials

In another embodiment, the compositions of the present invention comprise (a) nanoparticles comprising an active agent, wherein the nanoparticles have an average size of less than 500 nm; and (b) a resuspending material comprising a dextran polymer derivative; wherein the resuspending material constitutes from 5 wt % to 90 wt % of the combined mass of (1) the nanoparticles and (2) the resuspending material.

In one aspect, a dry, solid composition comprises (a) a plurality of nanoparticles comprising an active agent, and (b) a resuspending material comprising a dextran polymer derivative, or a pharmaceutically acceptable salt form thereof. As used herein, the term "dry, solid pharmaceutical composition" means that the composition is in a solid form and substantially free of liquids.

The solid pharmaceutical composition may take one of many configurations. In one embodiment, at least a portion of the nanoparticles in the solid composition are encapsulated by the resuspending material. By "at least a portion of the nanoparticles are encapsulated by the resuspending material" means that the resuspending material encapsulates at least a portion of the plurality of nanoparticles in the composition. The resuspending material may encapsulate only a portion of the nanoparticles, or may encapsulate essentially all of the nanoparticles in the composition. In one embodiment, the resuspending material encapsulates essentially all of the nanoparticles in the composition.

In one embodiment, the nanoparticles further comprise a poorly aqueous soluble polymer. In another embodiment, the poorly aqueous soluble polymer is a biocompatible polymer. In yet another embodiment, the poorly aqueous soluble polymer is a biodegradable polymer. In still another embodiment, the poorly aqueous soluble polymer is at least one of a biocompatible polymer and a biodegradable polymer. Exemplary poorly aqueous soluble polymers suitable for use in the nanoparticles include dextran polymer derivatives, vinyl polymers and co polymers, such as poly(vinyl acetate), poly(vinyl acetate-co-vinyl alcohol), and poly(ethylene-co-vinyl acetate); polylactones, such as poly(lactide), poly (glycolide), poly(mono-hexyl lactide), poly(di-hexyl lactide), poly($\epsilon$-caprolactone), and copolymers of these, including poly(lactide-co-glycolide), poly(lactide-co-$\epsilon$-caprolactone), poly(ethylene oxide-co-$\epsilon$-caprolactone), poly (ethylene oxide-co-lactide), and poly(ethylene oxide-co-lactide-co-glycolide); poly(alkyl)cyanoacrylates, such as poly (isobutyl)cyanoacrylate, and poly(hexyl)cyanoacrylate.

Thus, in one embodiment, the compositions may contain a plurality of nanoparticles, at least a portion of which are encapsulated by the resuspending material. Those nanoparticles not encapsulated by the resuspending material are in direct contact with the resuspending material.

In another embodiment, a portion of the resuspending material is adsorbed to the surface portion of the nanoparticles. The remaining portion of the resuspending material encapsulates the nanoparticles in the composition. In this embodiment, the resuspending material may act as a surface stabilizer, stabilizing the nanoparticles during the formation process or when present in aqueous suspension, reducing or preventing aggregation or flocculation of the nanoparticles prior to forming the solid composition of the invention, or when an aqueous solution is added to the solid nanoparticle composition in order to form an aqueous suspension of the nanoparticles.

In one embodiment, the dextran polymer derivative used as the resuspending material is aqueous soluble.

In another embodiment, the resuspending material is selected from the group consisting of dextran succinate, dextran acetate succinate, dextran propionate succinate, dextran acetate propionate succinate, and mixtures thereof and pharmaceutically acceptable salt forms thereof. By "pharmaceutically acceptable salt forms thereof" is meant the dextran polymer derivative is in a pharmaceutically acceptable salt form, or that the composition was formulated with the dextran polymer derivative in the presence of a counterion when the dry, solid pharmaceutical composition was formed. Exemplary counterions suitable for forming salt forms include sodium, potassium, ammonium, calcium, magnesium, aluminum, iron, and amines. In one embodiment, the dextran polymer derivative is in a sodium salt form, potassium salt form, or ammonium salt form.

In one embodiment, the dextran polymer derivative is in a pharmaceutically acceptable salt form. In this embodiment, the salt forms of these materials rapidly dissolve in a neutral pH aqueous environment, thereby producing a nanoparticle suspension when the dry, solid composition is administered to an aqueous solution.

The resuspending material constitutes from 5 wt % to 90 wt % of the combined mass of (1) the resuspending material and (2) the nanoparticles. The resuspending material is present in a sufficient amount so that a solid composition forms a nanoparticle suspension when administered to an aqueous use environment. Furthermore, a sufficient amount of resuspending material is present to prevent or retard agglomeration of the nanoparticles into larger particles following administration to an aqueous use environment. In one embodiment, the resuspending material constitutes from 10 wt % to 75 wt % of the combined mass of (1) the resuspending material and (2) the nanoparticles. In another embodiment, the resuspending material constitutes from 15 wt % to 50 wt % of the combined mass of (1) the resuspending material and (2) the nanoparticles. In still another embodiment, the resuspending material constitutes at least 10 wt % of the combined mass of (1) the resuspending material and (2) the nanoparticles. In still another embodiment, the resuspending material constitutes at least 20 wt % of the combined mass of (1) the resuspending material and (2) the nanoparticles. In yet another embodiment, the resuspending material constitutes at least 25 wt % of the combined mass of (1) the resuspending material and (2) the nanoparticles. In another embodiment, the resuspending material constitutes at least 40 wt % of the combined mass of (1) the resuspending material and (2) the nanoparticles. In another embodiment, the resuspending material constitutes at least 50 wt % of the combined mass of (1) the resuspending material and (2) the nanoparticles.

Compositions of Crystalline and Semi-Crystalline Active Agent

In another embodiment, the active agent is present in the dextran polymer derivative in the crystalline state. In yet another embodiment, the composition comprises particles that consist of single crystals of active agent coated with the dextran polymer derivative. In another embodiment, the composition comprises particles that consist of a plurality of crystals of active agent distributed in a continuous phase comprising the dextran polymer derivative. In still another embodiment, the active agent is in a form selected from at least one of crystalline and semi-crystalline active agent having a size of less than 400 nm in at least one dimension. In yet another embodiment, the active agent is distributed homogenously throughout the continuous phase comprising the dextran polymer derivative and optionally other excipients.

By "semi-crystalline" is meant crystalline active agent having the dextran polymer derivative incorporated into the crystals, crystals containing crystal defects, or semi-crystalline structures which take the form of sheets, tubes, or other structures in which the active agent is ordered but is not in the lowest solubility, bulk crystalline form alone. When the active agent is small crystals, the crystals need only be small in at least one dimension, but may be small in two or all three dimensions. The small crystals generally have less than about 200 crystal repeat units in at least one dimension. Although crystal repeat units can vary widely in size, they are generally less than about 2 nm in size and thus small crystals will generally be less than about 400 nm in at least one dimension. In one embodiment, the active agent is in the form of small crystals having a size of less than 200 nm in at least one dimension. In yet another embodiment, the active agent is in the form of small crystals having a size of less than 100 nm in at least one dimension.

In contrast, by "bulk crystalline form alone" is meant crystalline active agent in which the crystals exhibit long range order, for example, having at least about 200 repeat units in the shortest dimension, and in which no polymer is present.

In this embodiment, the active agent exhibits physical characteristics that are distinct from both active agent in the bulk crystalline form alone and active agent in a non-crystalline or amorphous form. One method for evaluating the physical characteristics of the active agent in the composition is powder x-ray diffraction. In this embodiment, the active agent in the composition, when characterized using powder x-ray diffraction, exhibits an x-ray diffraction pattern that is different than bulk crystalline active agent alone. Active agent that is present in a form selected from at least one of crystalline and semi-crystalline active agent having a size of less than 400 nm in at least one dimension, exhibits a diffraction pattern with reflections, scattering lines, or "peaks" that are broader, less well defined, smaller and/or missing compared to the reflections, scattering lines, or peaks present in the diffraction pattern of active agent in the bulk crystalline form alone. Throughout the remainder of this application, the term "peak" refers to the local maximum for a plot of scattered x-ray intensity versus scattering angle. For principal peaks, active agent in a form selected from at least one of crystalline and semi-crystalline active agent having a size of less than 400 nm in at least one dimension, may have a full width at half-height that is at least 1.1 fold that of the corresponding principal peak width at half-height for the active agent in bulk crystalline form alone. For example, if the full-width at half-height for the principal peak of crystalline active agent is 0.5°, the full-width at half-height of the corresponding principal peak of active agent which is present in a form selected from at least one of crystalline and semi-crystalline active agent having a size of less than 400 nm in at least one dimension, is at least 0.55°. By "principal peak" is meant a peak in the scattered x-ray intensity versus scattering angle plot that may be differentiated from the baseline and/or other peaks. The full-width at half-height may be even broader, and may be at least 1.25 fold, 2 fold or 3 fold or greater that of the corresponding principal peak of active agent in bulk crystalline form alone.

Peak widths may be compared for diffractograms from any conventional Powder X-ray Diffraction (PXRD) instrument. One such method for the collection of diffractograms would be to use a Bruker AXS D8 Advance diffractometer that is equipped with a Gobel mirror to focus the x-rays into a parallel beam, a Soller slit to reduce axial divergence of the beam before it impacts the sample, and a thin film attachment to collect only the properly diffracted x-rays at any specific collection angle. PXRD instruments functioning in such a manner should be capable of collecting data such that a 1.1-fold change in the width of a principal peak would be readily distinguishable from the random variation observed upon repeated measurement of the same sample.

Likewise, active agent present in a form selected from at least one of crystalline and semi-crystalline active agent having a size of less than 400 nm in at least one dimension, has a diffraction pattern that differs from pure amorphous (i.e., non-crystalline) active agent. The diffraction pattern for active agent present in a form selected from at least one of crystalline and semi-crystalline active agent having a size of less than 400 nm in at least one dimension, has some peaks, indicating some degree of crystallinity of the active agent. In contrast, active agent in the amorphous form exhibits no distinct peaks. Amorphous active agent may exhibit one or two extremely broad peaks, often termed "an amorphous halo." Active agent present in a form selected from at least one of crystalline and semi-crystalline active agent having a size of less than 400 nm in at least one dimension, exhibit one or more peaks that are narrower and extend above the amorphous halo.

Thermal techniques may also be used to characterize the state of the active agent. In general, the glass transition temperature (Tg) of a composition of active agent and polymer is a function of the amount of active agent that is in the amorphous form. For a composition comprising active agent present in both the amorphous form and in a form selected from at least one of crystalline and semi-crystalline active agent having a size of less than 400 nm in at least one dimension, only the active agent which is amorphous exhibits a Tg. When the glass transition temperature of the dextran polymer derivative is greater than that of the active agent, the Tg of a composition of active agent and dextran polymer derivative is greatest and near that of the polymer when all of the active agent is present in a form selected from at least one of crystalline and semi-crystalline active agent having a size of less than 400 nm in at least one dimension. That is, little, if any of the active agent is molecularly dispersed in the polymer as amorphous active agent. In contrast, the Tg of a composition of dextran polymer derivative and active agent is lowest when very little or none of the active agent in the composition is present in a form selected from at least one of crystalline and semi-crystalline active agent having a size of less than 400 nm in at least one dimension, but rather is dispersed throughout the polymer in the amorphous state. In such cases the Tg of the material approaches the Tg of a homogeneous solid amorphous dispersion consisting essentially of the active agent and polymer. Thus, by measuring the Tg of a composition of active agent and polymer, the percentage of active agent that is present in a form selected from at least one of crystalline and semi-crystalline active agent having a size of less than 400 nm in at least one dimension, and the percentage of active agent dispersed in the amorphous state may be determined. Differential scanning calorimetry (DSC) may be used to measure the glass transition temperature of such compositions.

The amount of active agent in the composition that is present in a form selected from at least one of crystalline and semi-crystalline active agent having a size of less than 400 nm in at least one dimension, may vary, but is generally greater than about 40 wt % of the active agent present in the composition. Any remaining active agent may be present in an amorphous form or crystalline form. In one embodiment, even higher percentages of active agent may be present in a form selected from at least one of crystalline and semi-crystalline active agent having a size of less than 400 nm in at least one dimension. Thus, in one embodiment, the amount of active agent present in a form selected from at least one of crystalline and semi-crystalline active agent having a size of less than 400 nm in at least one dimension, may be at least 50 wt %, at least 60 wt %, at least 75 wt %, or at least 90 wt % of the total amount of active agent in the composition.

Compositions comprising active agent and a dextran polymer derivative wherein the active agent is present in a form selected from at least one of crystalline and semi-crystalline active agent having a size of less than 400 nm in at least one dimension, may be prepared according to any technique that results in a solid having active agent present in a form selected from at least one of crystalline and semi-crystalline active agent having a size of less than 400 nm in at least one dimension. In one method, a solid dispersion of the active agent and dextran polymer derivative is initially formed, as described herein. In one embodiment, at least 90 wt % of the active agent in the solid dispersion is non-crystalline. The solid dispersion is then treated to increase the mobility of the active agent in the dispersion. By "mobility" is meant the movement or diffusion of the active agent through the dispersion. The initial solid amorphous dispersion may be treated by elevating the temperature of the dispersion, treating the dispersion with a mobility enhancing agent, or both. The mobility enhancing agent may be either a liquid or vapor. The mobility enhancing agent should be capable of plasticizing the dextran polymer derivative, or lowering the glass transition temperature of the dispersion. However, the mobility enhancing agent should not cause the active agent to become too soluble in the dispersion. The mobility enhancing agent lowers the glass transition temperature of the dispersion, thus increasing the mobility of the active agent in the dispersion. Suitable mobility enhancing agents include water, methanol, ethanol, propanol, butanol, carbon dioxide, acetone, methylethyl ketone, methyl iso-butyl ketone, acetonitrile, tetrahydrofuran, ethyl acetate, methylene chloride, toluene, and 1,1,1-trichloroethane, as well as mixtures of such materials.

In general, the compositions are prepared under conditions which cause the active agent to convert rapidly from the non-crystalline state to a form selected from at least one of crystalline and semi-crystalline active agent having a size of less than 400 nm in at least one dimension. Rapid conversion during treatment may cause the active agent to become "trapped" in small active agent-rich regions that are separated from one another by active agent-poor regions. In contrast, active agent that is allowed to crystallize slowly, especially at lower temperatures, will tend to form large crystals. Once a substantial portion of the active agent is present in active-agent-rich regions embedded or interspersed within the active agent-poor, polymer-rich regions, the mobility of the active agent is greatly decreased due to (1) the reduced concentration of active agent in the polymer-rich regions and (2) a decreased diffusion coefficient for the active agent in the polymer. This decrease in the diffusion coefficient of the active agent is particularly the case when the glass transition temperature of the non-crystalline active agent is less than the glass transition temperature of the dextran polymer derivative. This reduced active agent mobility prevents the active agent from aggregating into larger regions of active agent which may crystallize into larger, lower energy crystalline regions. The result is that the active agent becomes trapped in the polymer as small crystals of the active agent in a form selected from at least one of crystalline and semi-crystalline active agent having a size of less than 400 nm in at least one dimension.

Where the composition is formed by treating a solid dispersion, the initial solid dispersion of the active agent and dextran polymer derivative may be made according to any known process which results in at least a major portion (at least 60%) of the active agent being in a non-crystalline state. Exemplary mechanical processes include milling and extrusion; melt processes include high temperature fusion, solvent modified fusion and melt-congeal processes; and solvent processes include non-solvent precipitation, spray coating and spray drying.

Alternatively, other methods may be chosen for forming the compositions in which the active agent is converted into in a form selected from at least one of crystalline and semi-crystalline active agent having a size of less than 400 nm in at least one dimension, as the composition is formed. For example, such compositions may be formed by wet milling of the active agent using an aqueous solution of the dextran polymer derivative.

Delivery Routes and Methods of Treatment

In one embodiment, the invention provides a method of treating an animal, including humans, in need of therapy comprising administering a composition comprising an active agent and a dextran polymer derivative to an animal via a mode selected from the group consisting of oral, buccal, mucosal, sublingual, intravenous, intra-arterial, intramuscular, subcutaneous, intraperitoneal, intraarticular, infusion, intrathecal, intraurethral, topical, subdermal, transdermal, intranasal, inhalation, pulmonary tract, intratracheal, intraocular, ocular, intraaural, vaginal, and rectal.

In one embodiment, the composition comprising an active agent and a dextran polymer derivative is intended for oral, buccal, mucosal, or sublingual delivery. In this embodiment, the composition may be in the form of a powder that is incorporated into a suitable oral dosage form, such as tablets, capsules, caplets, multiparticulates, films, rods, suspensions, powders for suspension, and the like. Alternatively, the composition may be granulated prior to incorporation into a suitable dosage form.

In another embodiment, the composition comprising an active agent and a dextran polymer derivative is intended for intravenous, intra-arterial, intramuscular, subcutaneous, intraperitoneal, intraarticular, infusion, intrathecal, intraocular, or intraurethral delivery. In this embodiment, the composition may be in the form of a suspension or solution, suitable for injection via a needle, for introduction to an IV bag or bottle, or delivered via an appropriate catheter to the intended delivery site. In one embodiment, the composition is formulated as a dry powder or solid, that is then reconstituted into a suspension or solution prior delivery. Formulating the composition as a dry powder or solid typically improves the chemical and/or physical stability of the composition. The dry powder or solid is then mixed with a liquid, such as water suitable for injection or other liquid, to form a suspension or solution that may then be delivered via the chosen route. In still another embodiment, the composition is delivered in the form of a depot that controls or otherwise modifies the rate of release of active agent from the depot. The depot may be formed prior to delivery, or may be formed in situ after delivery. Such depots can be in the form of suspensions or can be in the form of a monolith such as a film or rod. The active agent may be released very rapidly by dissolution of the composition when a soluble or enteric or dispersible form of the dextran polymer derivative is used. Alternatively, the active agent may be released over hours, days, or even many months by utilizing a poorly aqueous soluble form of the dextran polymer derivative.

In another embodiment, the composition comprising an active agent and a dextran polymer derivative is intended for topical delivery. In this embodiment, the composition may be formulated into appropriate creams, transdermal patches, and the like, as is well-known in the art.

In another embodiment, the composition comprising an active agent and a dextran polymer derivative is intended for inhalation. As used herein, the term "inhalation" refers to delivery to a patient through the mouth and/or nose. In one embodiment, the dry powder suitable for inhalation is delivered to the "upper airways." The term "upper airways" refers to delivery to nasal, oral, pharyngeal, and/or laryngeal passages, including the nose, mouth, nasopharynx, oropharynx, and/or larynx. In another embodiment, the dry powder suitable for inhalation is delivered to the "lower airways." The term "lower airways" refers to delivery to the trachea, bronchi, bronchioles, alveolar ducts, alveolar sacs, and/or alveoli.

In one embodiment, the particles have a mass median aerodynamic diameter (MMAD) of 5 to 100 μm. In another embodiment, the particles have a MMAD of 10 to 70 μm. In yet another embodiment, the particles have an average diameter of 50 μm. In one embodiment, such particles are used in devices designed for delivery of particles to the upper airways. In another embodiment, such particles are used in devices designed for delivery of particles via the nose.

In one embodiment, the compositions may be formulated as a dry powder for use in a suitable inhalation device, such as a conventional dry powder inhaler. In another embodiment, the powders may be packaged in a packet suitable for insertion into a dry powder inhaler. Suitable dry powder inhalers typically rely on a burst of inspired air that is drawn through the unit to deliver the powder to the desired location. In another embodiment, the compositions may be administered as aqueous solutions or suspensions, or as solutions or suspensions in propellants, using, for example, a metered-dose inhaler. In this embodiment, the solution or suspension is aerosolized by liquid nebulizers employing either hydraulic or ultrasonic atomization. Compressor-driven nebulizers may also be employed, which may use a suitable propellant.

In another embodiment, the composition comprising an active agent and a dextran polymer derivative is intended for ocular or intraaural delivery. In this embodiment, the compositions may be formulated into appropriate suspensions, creams, fluids, drops or other suitable forms for administration.

In another embodiment, the composition comprising an active agent and a dextran polymer derivative is intended for vaginal or rectal delivery. In this embodiment, the compositions may be formulated into appropriate creams, pastes, suppositories or other suitable forms for administration.

For effective delivery, the compositions comprising the active agent and a dextran polymer derivative may be combined with other excipients and dosage form ingredients in essentially any manner that does not substantially alter the active agent's activity. The excipients may be either physically mixed with the compositions or included in the composition itself. Such formulation excipients are well known in the art as described in *Remington: The Science and Practice of Pharmacy* ($20^{th}$ Ed. 2000). Generally, excipients such as matrix materials, fillers, diluents, disintegrating agents, solubilizers, complexing agents, pigments, binders, lubricants, glidants, flavorants, and so forth may be used for customary purposes and in typical amounts without adversely affecting the properties of the compositions.

In one embodiment, a dosage form comprises the composition comprising the active agent and the dextran polymer derivative, wherein the composition comprising the active agent and dextran polymer derivative constitute at least 10 wt % of the dosage form. In some instances the dosage form constitutes even greater amounts of the composition comprising the active agent and dextran polymer derivative. Thus, the composition comprising the active agent and dextran polymer derivative may constitute at least 20 wt %, at least 30 wt %, at least 40 wt %, or even at least 50 wt % of the dosage form.

Other features and embodiments of the invention will become apparent from the following Examples that are given for illustrating the invention rather than for limiting its intended scope.

EXAMPLES

Dextran Polymer Derivatives

Polymer 1, dextran propionate succinate, having the degree of substitution shown in Table 1, was synthesized using the following procedures. First 90 g of dextran having a molecular weight of 10,000 daltons (available from Amersham Sciences, Piscataway, N.J.) was added to 495 g of formamide at 50° C. in a 1 L round bottom flask fitted with a glass jacket heated with mineral oil and an overhead mixer paddle stirring at 150 rpm. After 1 hour 30 g of sodium propionate was added to the mixture and stirred for 2.5 hours. To this, 195 g of propionic anhydride was added in 30 g increments over 30 minutes while the mixture stirred at 325 rpm. Finally, 13.5 g of succinic anhydride was added. After one hour the stir rate was reduced to 150 rpm and the solution was stirred overnight.

The polymer was precipitated by pumping 200 mL aliquots of polymer solution into a blender containing 1500 mL water and blended for 45 seconds. The solids were collected using a large Buchner funnel and Whatman type 113 filter paper. The solids were then washed in a 5 gallon plastic container containing 12 L water and stirred using an overhead mixer on a low setting for 20 minutes. The washed polymer was again filtered and collected as described above and blended in aliquots in the blender with water. The polymer/water mixture from the blender was placed into a 5 gallon plastic container with 7.5 L water and stirred by overhead mixing for 20 minutes. The polymer was collected by filtration as described above. The wash method was repeated twice more using the filtered polymer and 12 L water, stirring with overhead mixing for 20 minutes each time. Finally, the wet polymer was spread onto a tray and dried in a 40° C. oven overnight.

Reverse phase high-performance liquid chromatography (HPLC) was used to calculate the degree of substitution of propionate and succinate groups. For measurement of free acid content, polymer was dissolved in pH 7.4 phosphate buffer at a concentration of 12 mg/mL for 4 hours, then diluted 1:1 with 0.1% $H_3PO_4$ to a final pH of approximately 3. For measurement of propionate and succinate groups the polymer was hydrolyzed in 1N sodium hydroxide for 4 hours at a concentration of 3 mg/mL, and then diluted 1:1 to a final pH of approximately 3. HPLC analysis was performed on a Phenomenex Aqua C18 column with a pH 2.8 phosphate buffer eluent at a flow of 1 mL/min, and UV detection at 215 nm. Degree of substitution was calculated using the determined amount of anhydride and free acid of the propionate and succinate groups. Results from degree of substitution analysis are shown in Table 1.

Dynamic Vapor Sorption (DVS) was used to determine water uptake. The polymer was weighed into DVS pans in 10 to 50 mg aliquots. The polymer sample was equilibrated to 0% relative humidity (RH) in the DVS and weighed. The polymer sample was then equilibrated to 90% RH and weighed. Water uptake is the difference in mass of the sample at 90% RH and at 0% RH. The measured polymer properties are shown in Table 1. For comparison, the properties of underivatized dextran are included in Table 1 as Polymer C-1.

TABLE 1

| Polymer | Type* | Molecular Weight of Starting Dextran (daltons) | Acetate DS | Propionate DS | Succinate DS | Water Uptake at 90% RH (wt %) | Tg at 50% RH (° C.) |
|---|---|---|---|---|---|---|---|
| C-1 | Dextran | 10,000 | 0 | 0 | 0 | 26.8 | 46-50 |
| 1 | DPS | 10,000 | 0 | 1.9 | 0.23 | 8.4 | ND* |
| 2 | DAS | 10,000 | 1.6 | 0 | 0.3 | 8.5 | 75 |
| 3 | DPS | 3,000 | 0 | 1.8 | 0.6 | 7.7 | 34 |
| 4 | DPS | 5,000 | 0 | 1.8 | 0.4 | 7.3 | 72 |
| 5 | DPS | 20,000 | 0 | 1.8 | 0.2 | 7.8 | 85 |
| 6 | DAS | 10,000 | 2 | 0 | 0.5 | ND | ND |
| 7 | DS | 5,000 | 0 | 0 | 0.8 | ND | ND |
| 8 | DS | 5,000 | 0 | 0 | 1.3 | ND | ND |
| 9 | DS | 5,000 | 0 | 0 | 2.5 | ND | ND |
| 10 | DP | 5,000 | 0 | 0.8 | 0 | ND | ND |
| 11 | DP | 5,000 | 0 | 1.8 | 0 | ND | ND |
| 12 | DP | 10,000 | 0 | 1.3 | 0 | ND | ND |
| 13 | DPS | 10,000 | 0 | 1.3 | 0.2 | ND | ND |
| 14 | DPS | 5,000 | 0 | 0.5 | 0.7 | ND | ND |
| 15 | DAS | 10,000 | 1.6 | 0 | 0 | 8.7 | 60 |
| 16 | DPS | 5,000 | 0 | 0.5 | 0.4 | ND | ND |
| 17 | DPS | 10,000 | 0 | 2.3 | 0.8 | ND | 70 |
| 18 | DPS | 10,000 | 0 | 1.3 | 0.2 | ND | ND |
| 19 | DPS | 10,000 | 0 | 1.3 | 1.4 | ND | ND |

*Types: DP = dextran propionate; DA = dextran acetate; DS = dextran succinate; DPS = dextran propionate succinate; DAS = dextran acetate succinate; DAPS = dextran acetate propionate succinate
**ND = not determined.

Polymer 2, dextran acetate succinate, having the degree of substitution shown in Table 1, was synthesized using the following procedure. First 30 g of dextran having a molecular weight of 10,000 Daltons and 10 g of sodium acetate were added to 100 mL formamide at 50° C. in a glass container and magnetically stirred. To this, 60 g of acetic anhydride was added and stirred for 15 hours. Next, 8 g of succinic anhydride was added and the solution was stirred for 6 hours. After 21 hours the polymer was precipitated by pouring aliquots of the reaction mixture into 750 mL supersaturated brine in a blender. Allowed mixture to settle and recovered polymer to dry over night. After this, 350 mL of acetone was added to dissolve the polymer and separate out the salts. The mixture was re-precipitated in 750 mL acidified water and then copious amounts of sodium chloride were added and a yellow gummy substance on the top of the mixture was removed. All solids were re-dissolved in 250 mL acetone. The acetone was then removed by roto-evaporation. Finally, the polymer was collected by filtration and vacuum dried for several hours. HPLC degree of substitution determination and DVS analysis were performed as described for polymer 1.

The Tg of the polymer was determined using modulated differential scanning calorimetry (mDSC) as follows. Samples of the polymer (about 10 mg) were equilibrated at 50% RH overnight in an environmental chamber at ambient temperature. The samples were then loaded into pans and sealed inside the environmental chamber. The sample was then analyzed on a Q1000 mDSC (TA Instruments, New Castle, Del.). Samples were scanned over the temperature range of 0° C. to 200° C., at a scan rate of 2.5° C./min, and a modulation rate of ±1.5° C./min. The Tg was calculated based on half height. The Tg is also reported in Table 1.

Polymer 3, dextran propionate succinate, having the degree of substitution shown in Table 1, was synthesized using the following procedure. First dextran propionate was synthesized by adding 30 g of dextran having a molecular weight of 3,000 daltons to 150 mL formamide in a glass container and stirring magnetically until dissolved. To this, 10 g of sodium propionate was added and the mixture was heated to 50° C. Next, 50 g of propionic anhydride was added with vigorous stirring. The stir rate was reduced and the solution stirred overnight. The polymer was then precipitated by pouring the solution into a glass container containing 2500 mL water then saturating with sodium chloride. The solid polymer was collected and transferred to a small beaker. The aqueous portion was discarded and the residual solids left in the glass container were dissolved with 200 mL acetone and added to the collected polymer in the small beaker. This solution was precipitated into 2 L water and saturated with sodium chloride. The solids were collected and dissolved as described above. The mixture was combined with 200 mL isopropyl alcohol (IPA) and rotary evaporated to dryness. The remaining solids were dissolved in 100 mL acetone and vacuum filtered through a 5 μm nylon filter to remove salts. The acetone was removed by rotary evaporation and the remaining solids consisting of dextran propionate were dried under vacuum.

The dextran propionate described above (8.8 g total) was then dissolved in 80 mL propionic acid with 8.8 g sodium propionate and 2.6 g succinic anhydride, stirring at 85° C. for 7.5 hours. The heat was turned off and the mixture sat overnight. The polymer was precipitated by adding the solution to 800 mL rapidly stirred water in a 1 L beaker and then saturating the solution with sodium chloride. The precipitated polymer was collected and dissolved in 50 mL acetone. The rinse step was repeated twice more, and then 200 mL IPA was added and the solvent removed with rotary evaporation. The remaining solids were dried under vacuum. The solids were then dissolved into 200 mL acetone and vacuum filtered through a 0.2 μm nylon filter to remove salts. The remaining solution was rotary evaporated and the solids dried under vacuum.

HPLC degree of substitution determination and DVS analysis were performed as described for polymer 1.

Polymer 4, dextran propionate succinate, having the degree of substitution and water uptake shown in Table 1, was synthesized using the following procedure. First dextran propionate was synthesized by adding 468 g formamide to a reaction apparatus as described for Polymer 1, stirring at 180 rpm for 30 minutes. To this, 124 g dextran having a molecular weight of 5,000 daltons was added and stirred until dissolved. Next, 44 g sodium propionate was added and stirred until dissolved. Finally, 268 g propionic anhydride was added and the mixture stirred overnight. The solution was pumped from the reactor into a beaker using a peristaltic pump. Polymer was precipitated out of solution by quenching into water; 100 mL aliquots were added to 1.5 L water in a blender as described for polymer 1. The water layer was poured off and 1.5 L water was added to the precipitated polymer. The polymer was then blended for 1 minute. Next, the polymer was collected in a Buchner funnel with a Whatman 113 filter, and then placed in a 5 gallon container. After all 9 polymer aliquots were quenched and placed in the container, 10 L of water was added and the mixture was stirred for at least 15 minutes with an overhead stirrer. The solids were vacuum filtered as described above to remove the water. The large 10 L washes were repeated twice more. The solids consisting of dextran propionate were transferred to a tray lined with foil and dried overnight at 40° C. and 0 to 15% RH.

To form Polymer 4, 595 g propionic acid was then added to a 1 L reactor using the same apparatus as for dextran propionate synthesis, except that the jacket temperature was at 87° C. and the impellor was Teflon, stirring at 200 rpm. To this, 60 g of the above dextran propionate was added and stirred until dissolved. Next, 60 g of sodium propionate was added and stirred for 2 hours. Finally 18 g of succinic anhydride was added and stirred at 180 rpm for 2 hours. Solids were precipitated, blended, re-blended, washed, filtered and dried as described above.

HPLC degree of substitution determination and DVS analysis were performed as described for polymer 1.

Polymer 5, dextran propionate succinate, having the degree of substitution and water uptake shown in Table 1, was synthesized using the procedures described in synthesis of Polymer 4 except that dextran having a molecular weight of 20,000 daltons was used as the starting material.

HPLC degree of substitution determination and DVS analysis were performed as described for polymer 1.

Polymer 6, dextran acetate succinate, having the degree of substitution shown in Table 1, was synthesized using the following procedure. First 30 g of dextran having a molecular weight of 10,000 Daltons and 10 g of sodium acetate were added to 100 mL formamide at 50° C. in a glass container and magnetically stirred over night. To this, 75 g of acetic anhydride was slowly added and stirred over night. Next, 12 g of succinic anhydride was added and the solution was stirred for 6 hours. After 23 hours the polymer was precipitated by pouring aliquots of the reaction mixture into 750 mL acid/brine in a blender. Allowed mixture to settle and collected via Buchner funnel and filter. All solids were blended with 500 mL water. The solids were then collected by filtering through a Buchner funnel with filter paper. The solids were then dissolved in 350 mL acetone and stirred for 3 days. Precipitated aliquots of solution in acidified water and let settle. The solids were collected by filtering through a Buchner funnel and vacuum desiccated to dry.

HPLC degree of substitution determination was performed as described for polymer 1.

Polymer 7, dextran succinate, having the degree of substitution shown in Table 1, was synthesized using the following procedures. First 249.5 g of dextran having an average molecular weight of 5,000 Daltons (available from Pharmacosmos, Holbaek, Denmark) was added to 473.1 g of formamide at 50° C. in a 1 L round bottom flask fitted with a glass jacket heated with mineral oil and an overhead mixer paddle stirring at 150 rpm. After complete dissolution, typically less than 1 hr, 83.3 g of sodium propionate was added to the mixture and stirred for approximately 2 hours. To this, 79.5 g of succinic anhydride (Fluka Chemical) was added. After approximately 30 minutes a 51.3 g sample was removed using a peristaltic pump. To the remaining solution in the reactor, an additional 88.2 g of succinic anhydride was added. After 1 hr a 50 g sample was collected and washed as follows. Polymer 7 was precipitated using a 20:1 methanol to polymer ratio, two times, decanting the liquid between washes. The solid material was dried in a 40° C. oven overnight. The material was hardened and was milled with a mortar and pestle in methanol, and then washed with acetone, filtered, and re-dried.

Polymer 8, dextran succinate, having the degree of substitution shown in Table 1, was synthesized using the following procedures. To the solution remaining in the reactor after collection and isolation of Polymer 7 was added 68.7 g of succinic anhydride and allowed to react for approximately 1 hr. A 50.08 g sample was removed using a peristaltic pump and an additional 64.7 g succinic anhydride was added in combination with 51.4 g of propionic acid to increase solubility of the substrate. This reaction was allowed to proceed overnight and 50.1 g of polymer 8 was removed from the reactor. Polymer 8 (35 mL) was mixed with 700 mL of acetone at 250 rpm and up to 1400 rpm in a Silverson high shear mixer. The resultant particles were fine and did not settle quickly. The material was filtered and dried overnight at 40° C. The dried material was mixed to break up a thin film on the top of a fine powder, and re-dried.

Polymer 9, dextran succinate, having the degree of substitution shown in Table 1, was synthesized using the following procedures. To the solution remaining in the reactor after collection and isolation of Polymer 8 was added a 61.9 g aliquot of succinic anhydride and allowed to react to completion as judged by FTIR. The contents of the reactor (polymer 9) were removed by pumping into a glass vessel. Polymer 9 was washed at a 20:1 (g/g) acetone:polymer ratio in a Silverson high shear mixer at 2200 rpm and up to 5000 rpm. Small particles were obtained. Subsequent washes were performed using acetone. The polymer was filtered and dried overnight in a 40° C. oven. The dried material was remixed to break up a thin film on the top of a fine powder, and re-dried.

Polymer 10, dextran propionate, having the degree of substitution shown in Table 1, was synthesized using the following procedures. First 210 g of dextran having an average molecular weight of 5,000 Daltons (available from Pharmacosmos, Holbaek, Denmark) was added to 397.4 g of formamide (Sigma-Aldrich) at 50° C. in a 1 L round bottom flask fitted with a glass jacket heated with mineral oil and an overhead mixer paddle stirring at 300 rpm. After complete dissolution, 74.72 g of sodium propionate (Sigma Aldrich) was added to the mixture and stirred for approximately 1 hour. A background spectrum was collected using FTIR. To this, 196.3 g of propionic anhydride (Sigma Aldrich) was added while the mixture stirred at 325 rpm. After approximately 1 hour, when the reaction neared completion as judged by FTIR, a 50 g sample was removed from the reactor using a peristaltic pump.

The polymer was precipitated by washing twice with 400-500 mL each of acetone. For each wash, the polymer and acetone were thoroughly mixed using vortex and manual shaking. The solids were collected each time using a large Buchner funnel and Whatman type 113 filter paper. Finally, the wet polymer was spread onto a tray and dried in a 40° C. oven overnight. Any pellets found were crushed and dried further.

Polymer 11, dextran propionate, having the degree of substitution shown in Table 1, was synthesized using the following procedures. To the solution remaining in the reactor after collection and isolation of Polymer 10 was added a 79.4 g aliquot of propionic anhydride and the mixture was allowed to react to apparent completion as judged by FTIR (approximately 40 minutes). A 50 g sample was removed from the reactor. Propionic anhydride was added (61.7 g) and allowed to react to apparent completion. A 50 gram sample was removed by peristaltic pump, and isolated by washing twice with approximately 500 mL of water each time in a WaringPro 3 HP blender, and decanting of the liquid solution. The flocculated material was washed further in a 5 gallon bucket with approximately 5 L of water using an overhead stirrer. The polymer was collected by filtration using a large Buchner funnel and Whatman type 113 filter paper. The wet polymer was spread onto a tray and dried in a 40° C. oven overnight.

Polymer 12, dextran propionate, having the degree of substitution shown in Table 1, was synthesized using the following procedure. First 165 g of dextran having a molecular weight of 10,000 Daltons and 55 g of sodium propionate were added to 495 g formamide at 50° C. in a 1 L glass reactor equipped with a Heidolph mixer and pitched blade turbine. To this solution, 192.7 g of propionic anhydride was added and stirred at 150 rpm for 1.5 hours. The reaction went to completion as measured by FTIR. Next about 299 g of the reaction mixture was removed from the reactor and quenched in two aliquots by adding about 150 g of reaction mixture to 1.5 L water saturated with NaCl (e.g., brine). The mixture was blended in a blender, vacuum filtered using Watman filter paper to recover the polymer, and resuspended and washed with 1.7 L salt brine for 6 total washes. Upon completion of washing, the polymer was air dried, and then dissolved in about 500 gm of methanol. The salt crystals were filtered out of the methanol/polymer solution by vacuum filtration using a Watman glass microfibre filter. The final solution was clear methanol/polymer. This solution was spray dried in a Niro PSD-1 spray dryer and residual methanol was removed in a tray dryer for 24 hours at 40° C. and <10% RH. The final polymer was collected and analyzed for substitution as previously described.

Polymer 13, dextran propionate succinate, having the degree of substitution shown in Table 1, was synthesized using the following procedure. First 30 g of dextran having a molecular weight of 10,000 Daltons and 10 g of sodium propionate were added to 150 mL formamide at 50° C. in a glass container and magnetically stirred until dissolved. To this, 50 g of propionic anhydride was added and stirred for 30 minutes at 50° C. Next, 9 g of succinic anhydride was added and the solution was stirred overnight at 50° C. After 17.5 hours the polymer was precipitated by pouring aliquots of the reaction mixture into 750 mL pH 4 brine. This was followed by two washes of solids in 750 mL deionized water in a blender. The final wash in DI water was followed by complete dissolution of solids in 200 mL acetone. The solution was filtered through a 5 µm nylon filter. 50 mL of IPA was added and the IPA was then removed by rotoevaporation. Finally, the polymer was collected by filtration and dried under vacuum. The solids were then dissolved in 400 mL acetone and sent for spray drying.

HPLC degree of substitution determination was performed as described for polymer 1.

Polymer 14, dextran propionate succinate, having the degree of substitution shown in Table 1, was synthesized using the following procedures. First 140.0 g of dextran having an average molecular weight of 5,000 Daltons (available from Pharmacosmos, Holbaek, Denmark) was added to 265.1 g of formamide at 50° C. in a 1 L round bottom flask fitted with a glass jacket heated with mineral oil and an overhead mixer paddle stirring at 150 rpm. After complete dissolution 49.9 g of sodium propionate was added to the mixture and stirred for approximately 2 hours. To this, 106.7 g of propionic anhydride was added while the mixture stirred at 325 rpm. Finally, after approximately 30 minutes, 82.7 g of succinic anhydride was added. After one hour the stir rate was reduced to 150 rpm and the solution was stirred overnight.

The polymer (approximately 450 mL) was pumped into a glass vessel and washed at a 7:1 (v/v) ratio of acetone to polymer, four times. A stir bar was used for mixing, as well as manual shaking. The liquid was decanted in between washes. The solids were collected using a large Buchner funnel and Whatman type 113 filter paper. The polymer was spread onto a tray and dried in a 40° C. oven overnight.

Polymer 15, dextran acetate, having the degree of substitution shown in Table 1, was synthesized using the following procedure. First 30 g of dextran having a molecular weight of 10,000 Daltons and 11 g of sodium acetate were added to 100 mL formamide at 50° C. in a glass container and magnetically stirred until dissolved. To this, 60 g of acetic anhydride was added and stirred overnight at 50° C. Approximately 24 hours later, the reaction was precipitated into 2500 mL acidified (pH 4 with acetic acid) brine. The solution was filtered and a sticky polymer was collected. This was then re-dissolved in methanol. A small amount of IPA was added to the methanol solution and filtered. Small aliquots were added to ethyl acetate in two-1 L round bottom flasks. The remaining solvent was roto-evaporated off. The polymer was then dissolved in acetone, filtered and roto-evaporated again prior to recovery.

Degree of substitution determination was performed using NMR. DVS was performed as described for polymer 1.

Polymer 16, dextran propionate succinate, having the degree of substitution shown in Table 1, was synthesized using the following procedures. First 150.9 g of dextran having an average molecular weight of 5,000 daltons (available from Pharmacosmos, Holbaek, Denmark) was added to 286.1 g of formamide at 50° C. in a 1 L round bottom flask fitted with a glass jacket heated with mineral oil and an overhead mixer paddle stirring at 150 rpm. After complete dissolution 52.8 g of sodium propionate was added to the mixture and stirred for approximately 2 hours. To this, 110.8 g of propionic anhydride was added while the mixture stirred at 325 rpm. Finally, after approximately 30 minutes, 44.1 g of succinic anhydride was added. After 30 minutes the reaction appeared to be complete as judged by FTIR.

The polymer (approximately 460 mL) was pumped into a glass vessel and washed at a 7:1 (v/v) ratio of acetone to polymer, four times. A stir bar was used for mixing, as well as manual shaking. The liquid was decanted in between washes. The solids were collected using a large Buchner funnel and Whatman type 113 filter paper. The polymer was spread onto a tray and dried in a 40° C. oven overnight.

Polymer 17, dextran propionate succinate, having the degree of substitution shown in Table 1, was synthesized using the following procedures. First 822 g of dextran having a molecular weight of 10,000 daltons (available from Pharmacosmos) was added to 3104 g of formamide at 50° C. in a round bottom flask fitted with a glass jacket heated with mineral oil and an overhead mixer paddle stirring at 180 rpm. After approximately 1 hour, 293 g of sodium propionate was added to the mixture and stirred. To this, 1681 g of propionic anhydride was added and stirred.

Polymer 17 was precipitated by pumping 100 mL aliquots of polymer solution into a blender containing 750 mL water and blended. The solids were decanted and blended again in 750 mL water. The solids were collected using a large Buchner funnel with a paper filter. The solids were then washed in a 5 gallon vessel containing approximately 10 L water and stirred using an overhead mixer for 15 minutes. The washed polymer was again filtered and collected as described above and blended in aliquots in the blender with water. The polymer/water from the blender was placed into a 5 gallon vessel with 10 L water and stirred by overhead mixing for 15 minutes. This was collected by filtration as described above. The wash method was repeated twice more using the filtered polymer and 10 L water, stirring with overhead mixing for 15 minutes each time. Finally, the wet polymer was spread onto a tray and dried in a 40° C. (20% R.H.) oven overnight.

The dextran propionate described above (30 g) was then dissolved in 600 mL propionic acid with 30 g sodium propionate and 36 g succinic anhydride with stirring at 85° C., for 3 hours. Polymer was precipitated by adding a 200 mL aliquot of polymer solution into a blender containing 1.5 L water and blended. The first 1.5 L water was decanted and the polymer was blended again in 1.5 L water. The solids were collected using a large Buchner funnel with a paper filter. The solids were then washed in a 5 gallon vessel containing approximately 10 L water and stirred using an overhead mixer for 15 minutes. The washed polymer was again filtered and collected as described above and blended in aliquots in the blender with water. The chopped polymer/water from the blender was placed into a 5 gallon vessel with 10 L water and stirred by overhead mixing for 15 minutes. This was collected by filtration as described above. The wash method was repeated twice more using the filtered polymer and 10 L water, stirring with overhead mixing for 15 minutes each time. Finally, the wet polymer was spread onto a tray and dried in a 40° C. (20% R. H.) oven overnight.

The properties of Polymer 17 were measured using the procedures previously described, and are reported in Table 1.

Polymer 18, dextran propionate succinate, having the degree of substitution shown in Table 1, was synthesized using the following procedures. To the reaction mixture of Polymer 12 remaining after removal of 299 g to isolate Polymer 12, was added 13.36 g succinic anhydride. The solution was stirred at 150 rpm for 3 hours. Next, 340.6 g of the reaction mixture was removed from the reactor and quenched using water saturated with NaCl, as described above for Polymer 12. The polymer isolation and purification procedures were the same as described for Polymer 12, except that 1000 g methanol was used to dissolve Polymer 18.

Polymer 19, dextran propionate succinate, having the degree of substitution shown in Table 1, was synthesized using the following procedures. To the reaction mixture of Polymer 18 remaining after removal of 340.6 g to isolate Polymer 18, was added 32.2 g succinic anhydride. The solution was stirred at 150 rpm for 16 hours. Next, the reaction mixture was removed from the reactor and quenched using water saturated with NaCl. The polymer was washed six times with 1.7 L of water saturated with NaCl and vacuum filtered each time as described for Polymer 12. After the brine washes, Polymer 19 was washed once using water alone to remove the salt. Finally, the wet polymer was spread onto a tray and dried in a 40° C. oven overnight.

Active Agents Used in Examples

Active Agent 1 was S-(fluoromethyl) 6α,9-difluoro-11β, 17-dihydroxy-16α-methyl-3-oxoandrosta-1,4-diene-17β-carbothioate, 17-propionate, also known as fluticasone propionate, having the structure:

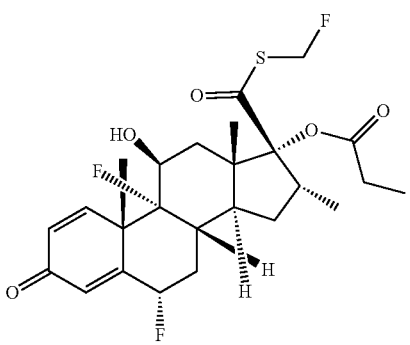

Active Agent 1 has a solubility of 0.4 μg/mL in pH 7.4 buffer, and a C Log P value of 3.7. The $T_g$ of amorphous Active Agent 1 was determined by DSC to be 84° C.

Active Agent 2 was propan-2-yl 2-{4-[(4-chlorophenyl)carbonyl]phenoxy}-2-methylpropanoate, also known as fenofibrate, having the structure

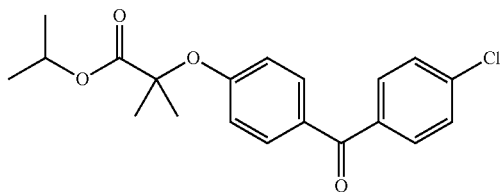 [SMILES: CC(C)OC(=O)C(C)(C)Oc1ccc(C(=O)c2ccc(Cl)cc2)cc1]

Active Agent 2 has a water solubility of about 0.8 μg/mL, a C Log P value of 5.2, and the Tm is 80.5° C.

Active Agent 3 was 3,5-dimethyl 2,6-dimethyl-4-(2-nitrophenyl)-1,4-dihydropyridine-3,5-dicarboxylate, also known as nifedipine, having the structure:

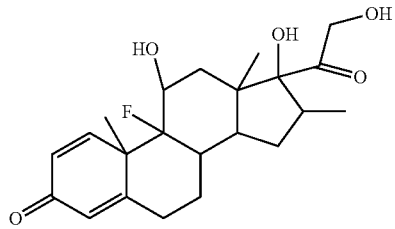 [SMILES: CC1CC2C3CCC4=CC(=O)C=CC4(C)C3(F)C(O)CC2(C)C1(O)C(=O)CO]

Active Agent 3 has a water solubility of 10 μg/mL, a C Log P value of 3.1, and the Tm is 173° C.

Active Agent 4 was 6-(trifluoromethoxy)benzothiazol-2-amine, also known as riluzole, having the structure

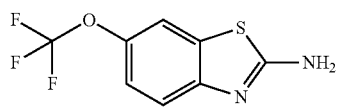 [SMILES: Nc1nc2ccc(OC(F)(F)F)cc2s1]

Active Agent 4 has a C Log P value of 3.2, and the Tm is 119° C. Active Agent 4 is sparingly soluble in 0.1 N HCl, and very slightly soluble in water and in 0.1 N NaOH.

Dispersions for Oral Delivery

Example 1

Active Agent 1:Polymer 1

A dry powder consisting of particles of a solid dispersion of Active Agent 1 was prepared by forming a spray solution containing 0.02 wt % Active Agent 1, 0.18 wt % Polymer 1, 94.81 wt % acetone, 4.99 wt % water as follows: the active agent and solvents were combined in a 30 L stainless steel tank and mixed to form a clear solution, then the polymer was added to the solution and mixed for 30 minutes.

The spray solution was pumped using a Bran & Luebbe (Norderstedt, Germany) metering pump from the 30-L tank to three Schlick (Düsen-Schlick GmbH of Untersiemau, Germany)) 1.5 pressure nozzles. Combined liquid feed was 100 g/minute, (33 g/min/nozzle) at 660 psig, into a Niro (Columbia, Md.) mobile minor Portable Spray-Drier ("PSD-1."). The PSD-1 was equipped with 9-inch and 4-inch chamber extensions to increase the vertical length of the dryer and the residence time of the particles in the drying chamber. The inlet drying nitrogen was flowing at 1370 g/min and heated to 135° C. and introduced to the spray drier equipped with a DHP gas disperser. The exit temperature of the drying gas and evaporated solvents was 55° C. The dried material was pneumatically conveyed through 2" ductwork to a 6-inch outside diameter cyclone. The resulting solid dispersion particles were collected in a container attached to the bottom of the cyclone via a butterfly valve.

The so-formed solid dispersion particles consisted of 10 wt % Active Agent 1 in Polymer 1. The particles were dried under a vacuum of less than about 0.2 atm for 12 hours at 22° C.

The dispersion was analyzed by powder X-ray diffraction (PXRD) using an AXS D8 Advance PXRD measuring device (Bruker, Inc. of Madison, Wis.) following the following procedure. Samples (approximately 100 mg) were packed in Lucite sample cups fitted with Si(511) plates as the bottom of the cup to give no background signal. Samples were spun in the φ plane at a rate of 30 rpm to minimize crystal orientation effects. The x-ray source (KCu$_α$, λ=1.54 Å) was operated at a voltage of 45 kV and a current of 40 mA. Data for each sample were collected over a period of 27 minutes in continuous detector scan mode at a scan speed of 1.8 seconds/step and a step size of 0.04°/step. Diffractograms were collected over the 2θ range of 4° to 40°. FIG. 1 shows the diffraction pattern of the dispersion of Example 1, revealing an amorphous halo, indicating the active agent in the dispersion was amorphous.

The Tg of the dispersion was determined using modulated differential scanning calorimetry (mDSC) as previously described. Samples of the dispersion (about 10 mg) were equilibrated at <5% RH overnight in an environmental chamber at ambient temperature. The dispersion had a single Tg of about 128° C., indicating the active agent in the dispersion was molecularly dispersed in the dextran polymer derivative.

In Vitro Dissolution Performance

The dispersion of Example 1 was tested using a syringe dissolution test. A sufficient amount of the composition of Example 1 was added to a syringe at a concentration of 50 μg/mL if all the active agent had dissolved. The syringe contained 20 mL of a buffer solution at pH 7.4, made by dissolving the following into 1 L of deionized water: 0.368 g calcium chloride (dihydrate), 0.203 g magnesium chloride (hexahydrate), 0.298 g potassium chloride (anhydrous), 6.0193 g sodium chloride, 2.604 g sodium bicarbonate (anhydrous), 0.097 g sodium citrate, 0.953 g sodium acetate, 0.142 g sodium phosphate (dibasic), and 0.0710 g sodium sulphate (anhydrous). This solution was adjusted to pH 7.42 by adding sufficient 0.1 N HCl. Next 0.1004 g of hydroxypropyl methyl cellulose (E3 grade) and 0.0197 g of L-alpha phosphatidyl choline, which had been dissolved in methanol and then the methanol removed by rotoevaporation, was added and the mixture stirred, then filtered through a 5 μm filter.

After adding the dispersion and the buffer to the syringe, the syringe was periodically inverted to mix the components in the syringe. The syringe was fitted with a 0.45 μm Supor PES syringe filter (manufacturer, city, state). After 5 minutes, 1 mL of fluid was pushed through the filter into a 2-mL centrifuge tube. A 0.5-mL aliquot of methanol was then added to the centrifuge tube, which was then inverted to mix the contents in the tube, followed by centrifugation at 13,000 rpm for 1 minute. The supernatant was transferred to another centrifuge tube. This procedure was repeated for all timepoints. Samples were frozen in liquid nitrogen and place on a lyophilizer for 3 days to remove all liquids. To the dried samples was added 100 μL 80/20 (w/w) methanol/water, then 250 μL methanol and the mixture shaken. Samples were then centrifuged at 13,000 rpm for 1 minute. Samples were then analyzed by high-performance liquid chromatography to determine the concentration of Active Agent 1 in the samples. The results are presented in Table 2.

TABLE 2

| Sample | Time (min) | Concentration (μg/mL) |
|---|---|---|
| Example 1 | 0 | 0 |
| | 5 | 12.6 |
| | 15 | 17.0 |
| | 30 | 13.5 |
| | 90 | 3.7 |
| | 180 | 0.3 |
| Control 1 | 0 | 0 |
| | 5 | 0.25 |
| | 15 | 0.30 |
| | 30 | 0.10 |
| | 90 | 0.24 |
| | 180 | 0.37 |

As a control (Control 1), the same test was performed using the same amount of crystalline Active Agent 1 alone, with no dextran polymer derivative. The results are also shown in Table 2.

The results of these tests are summarized in Table 3. These results show that the dispersion of Example 1 provided more than 40-fold improvement in $C_{max}$ compared to Control 1.

TABLE 3

| Example | $C_{max}$ (μg/mL) |
|---|---|
| 1 | 17.0 |
| Control 1 | 0.37 |

Dispersions for Pulmonary Delivery

Example 2

Active 1:Polymer 1

A dry powder consisting of particles of a solid dispersion of Active Agent 1 was prepared by forming a spray solution containing 0.02 wt % Active Agent 1, 0.18 wt % Polymer 1, 4.99 wt % water, and 94.81 wt % acetone as follows: the active agent and solvent were combined in a container and mixed to form a clear solution, then the polymer was added to the solution and mixed for 3 hours.

The spray solution was pumped from a 10-L stainless steel tank using a metering pump into a spray drier (a Niro type XP Portable Spray-Drier with a Liquid-Feed Process Vessel ("PSD-1")), equipped with 3 pressure nozzles (Schlick 1.5 60°; Dusen Schlick, GmbH of Untersiemau, Germany). The PSD-1 vessel was equipped with 9-inch and 4-inch chamber extensions to increase the vertical length of the dryer and residence time of the particles in the drying chamber. The inlet nitrogen gas at a flow of 1375 g/min was heated to 140° C. and introduced to the spray drier. The exit temperature of the drying gas was 55° C. The dried material was pneumatically conveyed through 2" ductwork to a cyclone. The resulting solid dispersion particles were collected in a 120 mL jar attached to the bottom of the cyclone via a 2" butterfly valve.

The so-formed solid dispersion particles were then dried under vacuum desiccation for 12 hours at room temperature.

In Vitro Inhalation Performance

The dry powder was tested using the NEXT GENERATION PHARMACEUTICAL IMPACTOR (NGI), Model 170 (available from MSP Corporation, Shoreview, Minn.). A 15 mg sample of the solid dispersion particles was evaluated using the NGI. The results of the NGI evaluation for Example 2 are shown in Table 4.

Differential Scanning Calorimetry (DSC)

DSC was used to measure the glass transition temperature. The solid dispersion samples were equilibrated for a minimum of 14 hours at ambient temperature and <5% RH. Sample pans were crimped and sealed in an environmental chamber, then loaded into a Thermal Analysis Q1000 Differential Scanning calorimeter equipped with an autosampler (available from TA Instruments, New Castle, Del.). The samples were heated by modulating the temperature at ±1.5° C./min, and ramping the temperature up to 200° C. at 2.5° C./min. The sample had a single Tg at 128° C. and no other thermal events, suggesting the composition was amorphous. This was confirmed by powder X-ray diffraction (PXRD) which showed an amorphous halo.

TABLE 4

| | NGI data | | Glass-Transition |
|---|---|---|---|
| Example | FPF* (%) | MMAD** (μm) | Temperature (° C.) (determined at 50% RH) |
| 2 | 72 | 2.9 | 128 |
| 3 | 75 | 2.6 | Not Determined |

*FPF—fine particle fraction (less than 4.6 μm)
**MMAD—mass median aerodynamic diameter Example 3

Active Agent 1:Polymer 9

A dry powder consisting of particles of a solid dispersion of Active Agent 1 was prepared by forming a spray solution containing 0.1 wt % Active Agent 1, 0.9 wt % Polymer 7, and 99 wt % acetone as follows: the active agent and solvent were combined in a container and mixed to form a clear solution, then the polymer was added to the solution and mixed for 3 hours.

The spray solution was pumped from a 6 L container using a peristaltic pump into a spray drier (a Niro type XP Portable Spray-Drier, PSD-1), equipped with a 2-fluid nozzle (spray systems: liquid is 2050 and air is 120). The PSD-1 vessel was equipped with 9-inch and 4-inch chamber extensions to increase the vertical length of the dryer and residence time of the particles in the drying chamber. The inlet nitrogen gas at a flow of 920 g/min was heated to 110° C. and introduced to the spray drier. The exit temperature of the drying gas was 45° C. The dried material was pneumatically conveyed through 2" ductwork to a cyclone. The resulting solid dispersion particles were collected in a 500 mL jar attached to the bottom of the cyclone via a 2" butterfly valve.

The so-formed solid dispersion particles were then dried under vacuum desiccation for 12 hours at room temperature.

The dry powder was tested using the NEXT GENERATION PHARMACEUTICAL IMPACTOR (NGI), Model 170 (available from MSP Corporation, Shoreview, Minn.), using the procedures described in Example 2. The results are summarized in Table 4.

Example 4

In Vivo of Example 3 Formulation

The dry powder of Example 3 was used in an in vivo test to determine the concentration of Active Agent 1 in the lung, bronchoalveolar lavage fluid (BALF) and plasma of male Sprague Dawley rats after a single inhalation exposure to one of three dose levels of an aerosolized dry powder. Aerosols of the dry powder of Example 3 were generated with a Palas Rotating Brush Generator (RGB) 1000 solid particle disperser (Palas GmbH; Karlsruhean, Germany). The dry powder of Example 3 was loaded into a 14-mm piston and gently packed prior to integration on to the RBG 1000. The RGB 1000 was operated with a brush rotation speed of 1200 revolution/min and a brush feed speed of between 15 and 30 mm/h. Compressed air was added to a final volumetric flow rate of approximately 19.5 L/min. Aerosols were directed through approximately 24 in of a 1.58-cm (diameter) delivery line. Aerosols transited into a flow-past 36-port nose-only rodent exposure chamber. The chamber exhaust flow rate was adjusted to a volumetric flow rate of approximately 22 L/min, slightly higher than the flow rate supplied by the rotating brush aerosol generator.

Prior to dosing, aerosols were collected (from the exposure plenum) on 47-mm Zefluor filters (PALL Life Sciences; Ann Arbor, Mi) at a nominal volumetric flow rate of 0.5 L/min. Particle size distribution was measured using an aerodynamic particle sizer (APS; TSI Model 3321; Shoreview, Minn.). The MMAD for the dry powder of Example 3 using this aerosol generation technique was determined to be 2.3 µm with a geometric standard deviation (GSD) of 1.6. The concentration of Active Agent 1 in the aerosols was determined to range from 0.4 to 0.8 mg/L.

Eighty-one (81) male Sprague Dawley rats were exposed to the dry powder of Example 3 at target concentrations of 0.1, 1.0, and 2.0 mg/L for 30 minutes, to achieve target doses of 2, 20, and 40 mg/kg, respectively. Animals were sacrificed at nine specified time points post exposure and blood (plasma), BALF, and lungs were harvested. Samples were stored at approximately −70° C. before and after analysis. Concentrations of Active Agent 1 were determined using an LC/MS/MS method, following liquid-liquid extraction. Tables 5 and 6 summarize the results.

TABLE 5

| Time (hr) | Dose (mg/kg) | | |
|---|---|---|---|
| | 2 | 20 | 40 |
| Drug Concentration in Plasma (ng/mL) | | | |
| 0.083 | 3.85 ± 0.77 | 31.9 ± 3.0 | 90.9 ± 8.4 |
| 0.25 | 2.24 ± 0.41 | 23.9 ± 1.8 | 80.1 ± 15.8 |
| 0.5 | 1.93 ± 0.24 | 16.2 ± 1.8 | 49.7 ± 20.2 |
| 1 | 1.59 ± 0.43 | 10.5 ± 1.1 | 29.8 ± 1.5 |
| 2 | 1.17 ± 0.76 | 9.8 ± 2.1 | 18.2 ± 4.6 |
| 4 | 0.41 ± 0.08 | 4.1 ± 2.3 | 7.9 ± 1.9 |
| 8 | 0.13 ± 0.01 | 1.2 ± 0.5 | 2.8 ± 1.2 |
| 12 | 0 ± 0 | 0.54 ± 0.15 | 1.5 ± 1.1 |
| 24 | 0.12 ± 0.13 | 0.18 ± 0.18 | 0.28 ± 0.14 |
| Drug Concentration in BALF (ng/mL) | | | |
| 0.083 | 2.8 ± 1.9 | 23.9 ± 17.1 | 102 ± 30 |
| 0.25 | 0 ± 0 | 10.7 ± 1.5 | 110 ± 32 |
| 0.5 | 0 ± 0 | 5.3 ± 2.1 | 22.8 ± 22 |
| 1 | 0 ± 0 | 4.4 ± 1.7 | 10.4 ± 7.8 |
| 2 | 0 ± 0 | 1.9 ± 0.2 | 2.5 ± 1.3 |
| 4 | 0 ± 0 | 0 ± 0 | 0 ± 0 |
| 8 | 0 ± 0 | 0 ± 0 | 0 ± 0 |
| 12 | 0 ± 0 | 0 ± 0 | 0 ± 0 |
| 24 | 0 ± 0 | 0 ± 0 | 0 ± 0 |
| Drug Concentration in the Lungs (ng/mL) | | | |
| 0.083 | 37.5 ± 12.8 | 387 ± 333 | 773 ± 144 |
| 0.25 | 20.1 ± 8.7 | 104 ± 66 | 511 ± 296 |
| 0.5 | 15.6 ± 5.7 | 45.7 ± 8.8 | 200 ± 110 |
| 1 | 16.1 ± 10.1 | 48.7 ± 20.8 | 186 ± 68 |
| 2 | 8.1 ± 1.4 | 27.6 ± 4.3 | 73.9 ± 36.8 |
| 4 | 3.4 ± 1.0 | 28.1 ± 14 | 22 ± 3.9 |
| 8 | 0.74 ± 0.64 | 7.5 ± 4.4 | 10.3 ± 3.2 |
| 12 | 0 ± 0 | 2.01 ± 0.8 | 4.6 ± 1.1 |
| 24 | 0.74 ± 1.3 | 0.35 ± 0.61 | 0.99 ± 0.89 |

TABLE 6

| Formulation | Max Dose (mg/kg) | $C_{max}$ (ng/mL) | $T_{max}$ (hr) | $AUC_{0-12\ hr}$ (ng * hr/mL) |
|---|---|---|---|---|
| Example 3 | 0.1 | 3.9 | 0.58 | 6 |
| | 1 | 32 | 0.58 | 58 |
| | 2 | 96 | 0.58 | 139 |

$AUC_{0-12\ hr}$ = area under the concentration versus time curve from 0 to 12 hours.

Nanoparticle Examples

Example 5

Active Agent 2:Polymer 17

For Example 5, nanoparticles containing Active Agent 2 were prepared as follows. First, 1.0 mg Active Agent 2 and 9.0 mg Polymer 17 were dissolved in 5 mL ethyl acetate to form an organic solution. Next, 2.5 mg sodium glycocholate (NaGly) was dissolved in 5 mL deionized water to form an aqueous solution. The organic solution was then poured into the aqueous solution and emulsified for 3 min using a Kinematica Polytron 3100 rotor/stator (Kinematica AG, Lucerne, Switzerland) at 10,000 rpm (high-shear mixing). The solution was further emulsified using a Microfluidizer (Microfluidics [Newton, Mass.] model M-110S F12Y with ice bath and cooling coil), for about 6 minutes at 12,500 psi (high-pressure homogenization). The ethyl acetate was removed from the emulsion using a rotary evaporator, resulting in an aqueous suspension of nanoparticles, with a composition ratio of 1:9:2.5 Active Agent 2:Polymer 17:NaGly.

A filter potency test was used to measure the stability of the nanoparticle suspension. Changes in potencies due to particle agglomeration were measured over time using HPLC. The initial potency of the unfiltered aqueous nanoparticle suspension was first measured using HPLC. The suspension was allowed to stand at room temperature undisturbed to determine suspension stability. After 4 hours and after 24 hours, the suspension was filtered using a 1 μm filter and a 50 μL sample was added to 1 mL methanol and analyzed by HPLC. HPLC analysis of Active Agent 2 was performed using a Zorbax RX-$C_{18}$ column. The mobile phase consisted of 20/80 10 mM ammonium acetate/acetonitrile. UV absorbance was measured at 260 nm.

Percent potency remaining was calculated by dividing the filtered concentration at each time by the initial unfiltered concentration. Suspensions were also examined using optical microscopy. The results are shown in Table 7. The results in Table 7 show that 91% of the potency of the nanoparticle suspension of Example 5 is maintained following filtration by a 1 μm filter after 24 hours. These results demonstrate that the nanoparticle suspension of Example 5 was stable during storage with no measurable particle agglomeration.

TABLE 7

| Example 5 | DLS of Unfiltered Suspension (nm) | HPLC Potency (1 μm filtered) (%) | Microscopy |
|---|---|---|---|
| Initial | 159 | 99 | No crystals |
| 4 hours | 146 | 92 | No crystals |
| 24 hours | 156 | 91 | No crystals |

Example 6

Active Agent 3:Polymer 1

For Example 6, nanoparticles containing Active Agent 3 were prepared as follows. First, 1.0 mg Active Agent 3 and 9.0 mg Polymer 17 were dissolved in 5 mL ethyl acetate to form an organic solution. Next, 2.5 mg sodium glycocholate (NaGly) was dissolved in 5 mL deionized water to form an aqueous solution. The organic solution was then poured into the aqueous solution and emulsified for 3 min using a Kinematica Polytron 3100 rotor/stator (Kinematica AG, Lucerne, Switzerland) at 10,000 rpm (high-shear mixing). The solution was further emulsified using a Microfluidizer (Microfluidics [Newton, Mass.] model M-110S F12Y with ice bath and cooling coil), for about 6 minutes at 12,500 psi (high-pressure homogenization). The ethyl acetate was removed from the emulsion using a rotary evaporator, resulting in an aqueous suspension of nanoparticles, with a composition ratio of 1:9:2.5 Active Agent 3:Polymer 17:NaGly. DLS analysis resulted in an average diameter of 191 nm with a polydispersity of 0.14.

A filter potency test was used to measure the stability of the nanoparticle suspension. Changes in potencies due to particle agglomeration were measured over time using HPLC. The initial potency of the unfiltered aqueous nanoparticle suspension was first measured using HPLC. The suspension was allowed to stand at room temperature undisturbed to determine suspension stability. After 4 hours and after 22 hours, the suspension was filtered using a 1 filter and a 50 μL sample was added to 1 mL methanol and analyzed by HPLC.

Percent potency remaining was calculated by dividing the filtered concentration at each time by the initial unfiltered concentration. Suspensions were also examined using optical microscopy. The results are shown in Table 8. The results in Table 8 show that 91% of the potency of the nanoparticle suspension of Example 6 is maintained following filtration by a 1 μm filter after 22 hours. These results demonstrate that the nanoparticle suspension of Example 6 was stable during storage with no measurable particle agglomeration.

TABLE 8

| Example 6 | DLS of Unfiltered Suspension (nm) | HPLC Potency (1 μm filtered) (%) | Microscopy |
|---|---|---|---|
| Initial | 191 | 100 | No crystals |
| 4 hours | 165 | 95 | No crystals |
| 24 hours | 156 | 95 | No crystals |

Resuspension Examples

Examples 7-9

Examples 7-9 demonstrate resuspension of nanoparticles using dextran polymer derivatives. For these examples, nanoparticles containing Active Agent 4 were prepared as follows. First, 100 mg Active Agent 4 and 300 mg ethylcellulose (ETHOCEL™) were dissolved in 6 mL ethyl acetate to form an organic solution. Next, 20 mg sodium taurocholate (NaTC) was dissolved in 20 mL deionized water to form an aqueous solution. The organic solution was then poured into the aqueous solution and emulsified for 3 min using a Kinematica Polytron 3100 rotor/stator (Kinematica AG, Lucerne, Switzerland) at 10,000 rpm (high-shear mixing). The solution was further emulsified using a Microfluidizer (Microfluidics [Newton, Mass.] model M-110S F12Y with ice bath and cooling coil), for about 6 minutes at 12,500 psi (high-pressure homogenization). The ethyl acetate was removed from the emulsion using a rotary evaporator, resulting in an aqueous suspension of nanoparticles, with a composition ratio of 10:30:2 Active Agent 4:ethylcellulose:NaTC. The particle size of the nanoparticles in the aqueous suspension was determined using dynamic light scattering (DLS). The average diameter was found to be 100±35 nm.

For storage in powder form, nanoparticles were lyophilized with an aqueous solution containing a dextran polymer derivative. Example 7 was formed using Polymer 18, Example 8 was formed using Polymer 19, and Example 9 was formed using Polymer 16. To obtain the dried nanoparticles, 1.5 mL of aqueous solution containing 60 mg polymer (40 mg/mL) (adjusted to pH 7.4), was added to 3 mL aqueous nanoparticle suspension (15 mg/mL), and the suspension was lyophilized overnight to obtain a dry powder. The composition ratio of the dried nanoparticles was about 1:1.3 nanoparticles:dextran polymer derivative.

For comparison, the aqueous nanoparticle suspension was lyophilized without a dextran polymer derivative (Control 1).

Once a solid powder was obtained, the formulations of Examples 7-9 and Control 1 were added to 4.5 mL deionized water at a concentration of about 2 mg Active Agent 4/mL and the resulting suspension was vortexed 1 minute. Filter potency was used to examine agglomeration of nanoparticles in the suspension. As nanoparticles agglomerate, the larger particles are removed via filtration, and the concentration of suspended active agent is reduced.

To measure nanoparticle potency, 50 μL of the aqueous nanoparticle suspension was added to 1 mL methanol and analyzed by high-performance liquid chromatography (HPLC). HPLC analysis of Active Agent 4 was performed using a Zorbax SB $C_8$ column. The mobile phase consisted of 45% 10 mM ammonium acetate, adjusted to pH 4, and 55% acetonitrile. UV absorbance was measured at 254 nm. Next, the suspension was filtered using a 0.2 μm filter and analyzed again using HPLC. Percent potency remaining was calculated by dividing the filtered concentration by the unfiltered concentration. The results are shown in Table 9, and the data indicate that the nanoparticles remain small and unagglomerated following resuspension.

TABLE 9

| Sample | Formulation | Particle Size of Unfiltered Suspension (nm) | HPLC Potency 0.2 μm filtered/ unfiltered (wt %) |
|---|---|---|---|
| Example 7 | Active Agent 4:Ethocel:NaTC:Polymer 18 10:30:2:55 | 100 nm ± 15 nm | 98 |
| Example 8 | Active Agent 4:Ethocel:NaTC:Polymer 19 10:30:2:55 | 120 nm ± 40 nm | 81 |
| Example 9 | Active Agent 4:Ethocel:NaTC:Polymer 16 10:30:2:55 | 115 nm ± 40 nm | 88 |
| Control 1 | Active Agent 4:Ethocel:NaTC 10:30:2 | poor fit (suspension precipitated) | 1 |

Examples with Small Crystalline Drug/Semi-Crystalline Drug

Example 10

An active agent may be formed into a solid dispersion using a dextran polymer derivative (such as Polymer 1), for example, by using the process described in Example 1. The active agent in the dispersion may be 10 wt % to 50 wt % of the total mass of the dispersion. More than 90 wt % of the active agent in the dispersion may be in a non-crystalline or amorphous form.

The dispersion may then be exposed to elevated temperature (e.g., at least 40° C.) and humidity (e.g., at least 50% relative humidity) for a period of time ranging from 4 hours to 72 hours. The resulting material forms small crystals of active agent or semi-crystalline active agent with characteristic diameters of less than about 400 nm as measured by transmission electron microscopy (TEM) analysis, or shows broadened or missing peaks relative to pure active agent when analyzed via PXRD.

In a disclosed embodiment, a pharmaceutical composition comprises (a) from 0.01 to 99 wt % of an active agent; and (b) from 1 to 99.99 wt % of a dextran polymer derivative, wherein said dextran polymer derivative is selected from dextran acetate, dextran propionate, dextran succinate, dextran acetate propionate, dextran acetate succinate, dextran propionate succinate, dextran acetate propionate succinate, and mixtures thereof. In some embodiments, said dextran polymer derivative is selected from the group consisting of dextran acetate, dextran propionate, dextran succinate, dextran acetate propionate, dextran acetate succinate, dextran propionate succinate, dextran acetate propionate succinate, and mixtures thereof.

In another disclosed embodiment, a pharmaceutical composition comprises (a) from 0.01 to 99 wt % of an active agent; and (b) from 1 to 99.99 wt % of a dextran polymer derivative, wherein said dextran polymer derivative is selected from dextran acetate, dextran propionate, dextran succinate, dextran acetate propionate, dextran acetate succinate, dextran propionate succinate, dextran acetate propionate succinate, and mixtures thereof, wherein said active agent and said dextran polymer derivative constitute at least 50 wt % of said composition. In certain embodiments, said dextran polymer derivative is selected from the group consisting of dextran acetate, dextran propionate, dextran succinate, dextran acetate propionate, dextran acetate succinate, dextran propionate succinate, dextran acetate propionate succinate, and mixtures thereof, wherein said active agent and said dextran polymer derivative constitute at least 50 wt % of said composition. In some embodiments, at least 50 wt % of said composition is comprised of said active agent and said dextran polymer derivative. In other embodiments, at least 75 wt % or at least 90 wt % of said composition consists essentially of said active agent and said dextran polymer derivative.

In any or all of the above embodiments, the composition may consist essentially of said active agent and said dextran polymer derivative. In any or all of the above embodiments, the composition may comprise a plurality of particles comprising said active agent and said dextran polymer derivative. The composition may be in the form of a coating on a substrate.

In any or all of the above embodiments, the composition may be in the form of a solid dispersion of said active agent and said dextran polymer derivative, wherein at least 90 wt % of said active agent in said dispersion is non-crystalline. The composition may be in the form of a solid solution of said active agent and said dextran polymer derivative.

Alternatively, the composition may be in the form of nanoparticles comprising said active agent and said dextran polymer derivative, wherein said nanoparticles have an average size of less than 500 nm.

In other embodiments, the composition may comprise a) nanoparticles comprising said active agent, wherein said nanoparticles have an average size of less than 500 nm; and (b) a resuspending material comprising said dextran polymer derivative; from 5 wt % to 90 wt % of the combined mass of (1) said nanoparticles and (2) said resuspending material comprises said resuspending material.

In still other embodiments, said active agent is present in said dextran polymer derivative in a form selected from at least one of crystalline and semi-crystalline active agent having a size of less than 400 nm in at least one dimension.

In any or all of the above embodiments, the dextran polymer derivative is aqueous soluble over at least a portion of the pH range of 1-8. Alternatively, the dextran polymer derivative may be poorly aqueous soluble over at least a portion of the pH range of 1-8. In some embodiments, the dextran polymer derivative is an enteric polymer.

In any or all of the above embodiments, the dextran polymer derivative is selected from dextran succinate, dextran acetate succinate, dextran propionate succinate, dextran acetate propionate succinate, and mixtures thereof. In certain embodiments, the dextran polymer derivative is selected from the group consisting of dextran succinate, dextran acetate succinate, dextran propionate succinate, dextran acetate propionate succinate, and mixtures thereof. In some embodiments, said dextran polymer derivative is selected from dextran acetate succinate, dextran propionate succinate, dextran acetate propionate succinate, and mixtures thereof. In certain embodiments, said dextran polymer derivative is selected from the group consisting of dextran acetate succinate, dextran propionate succinate, dextran acetate propionate succinate, and mixtures thereof.

In any or all of the above embodiments, the dextran polymer derivative may have the following degree of substitution (DS) for acetate, propionate, and succinate substituents: $DS_{acetate}$ ranges from 0 to 2.8; $DS_{propionate}$ ranges from 0 to 2.8; and $DS_{succinate}$ ranges from 0 to 2.8. In some embodiments, said degree of substitution for succinate is at least 0.05.

In any or all of the above embodiments, the dextran polymer derivative may have a molecular weight ranging from 3000 daltons to 100,000 daltons or from 3000 daltons to 70,000 daltons.

In some of the above embodiments, the pharmaceutical composition is formulated for oral delivery, and said dextran polymer derivative is at least one of aqueous soluble and enteric. In other embodiments, the composition is formulated for inhalation, and said dextran polymer derivative is at least one of aqueous soluble and enteric. In still other embodiments, the composition is formulated for parenteral delivery, and said dextran polymer derivative is at least one of poorly aqueous soluble and enteric. In other embodiments, the composition is formulated for intravenous delivery, and said dextran polymer derivative is at least one of poorly aqueous soluble and enteric. In yet other embodiments, the composition is formulated for ocular delivery, and said dextran polymer derivative is at least one of poorly aqueous soluble and enteric.

In some of the above embodiments, the dextran polymer derivative is dextran acetate. In other embodiments, the dextran polymer derivative is dextran propionate, or dextran succinate, or dextran acetate propionate, or dextran acetate succinate, or dextran propionate succinate, or dextran acetate propionate succinate.

A dosage form may comprise the composition of any one of the above embodiments, wherein at least 5 wt % of said dosage form is comprised of said composition. In some embodiments, at least 10 wt % of said dosage form, or at least 20 wt % of said dosage form, or at least 25 wt % of said dosage form consists essentially of said composition. In certain embodiments, the dosage form is in the form of a dry powder, or a tablet or capsule, or a suspension.

A method of treating an animal in need of therapy comprises administering the composition of any one of the above embodiments to an animal via a mode selected from oral, buccal, mucosal, sublingual, intravenous, intra-arterial, intramuscular, subcutaneous, intraperitoneal, intraarticular, infusion, intrathecal, intraurethral, topical, subdermal, transdermal, intranasal, inhalation, pulmonary tract, intratracheal, intraocular, ocular, intraaural, vaginal, and rectal. In some embodiments, the composition is administered to an animal via a mode selected from the group consisting of oral, buccal, mucosal, sublingual, intravenous, intra-arterial, intramuscular, subcutaneous, intraperitoneal, intraarticular, infusion, intrathecal, intraurethral, topical, subdermal, transdermal, intranasal, inhalation, pulmonary tract, intratracheal, intraocular, ocular, intraaural, vaginal, and rectal.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A pharmaceutical composition comprising:
   (a) from 0.01 to 99 wt % of an active agent; and
   (b) from 1 to 99.99 wt % of a biocompatible dextran polymer derivative comprising succinate groups and having a degree of substitution for succinate ($DS_{succinate}$) of at least 0.05,
   wherein said dextran polymer derivative is selected from
      dextran succinate,
      dextran acetate succinate,
      dextran propionate succinate,
      dextran acetate propionate succinate, and
      mixtures thereof, and wherein said dextran polymer derivative is water soluble above pH 5.

2. The composition of claim 1 wherein said composition consists essentially of said active agent and said dextran polymer derivative.

3. The composition of claim 1 wherein said dextran polymer derivative is an enteric polymer having an aqueous solubility of less than 0.1 mg/mL at a pH of about 3.0 or less, and an aqueous solubility of at least 1 mg/mL at a pH of greater than about 7.

4. The composition of claim 1 wherein said composition constitutes a plurality of particles comprising said active agent and said dextran polymer derivative.

5. The composition of claim 1 in the form of a solid dispersion of said active agent and said dextran polymer derivative, wherein at least 90 wt % of said active agent in said dispersion is non-crystalline.

6. The composition of claim 1 in the form of nanoparticles comprising said active agent and said dextran polymer derivative, wherein said nanoparticles have an average size of less than 500 nm.

7. The composition of claim 1 wherein said composition comprises
   (a) nanoparticles comprising said active agent, wherein said nanoparticles have an average size of less than 500 nm; and
   (b) a resuspending material comprising said dextran polymer derivative,
wherein said resuspending material constitutes from 5 wt % to 90 wt % of the combined mass of (1) said nanoparticles and (2) said resuspending material.

8. The composition of claim 1 wherein said active agent is present in said dextran polymer derivative in a form selected from at least one of crystalline and semi-crystalline active agent having a size of less than 400 nm in at least one dimension.

9. The composition of claim 1 wherein:
   (i) said dextran polymer derivative is dextran succinate and the $DS_{succinate}$ is from 0.05 to 2.8;
   (ii) said dextran polymer derivative is dextran acetate succinate, the $DS_{succinate}$ is from 0.05 to 1.5, and $DS_{acetate}$ is from 0.25 to 2.5;
   (iii) said dextran polymer derivative is dextran propionate succinate, the $DS_{succinate}$ is from 0.05 to 1.5, and $DS_{propionate}$ is from 0.1 to 2.5; or
   (iv) said dextran polymer derivative is dextran acetate propionate succinate, the $DS_{succinate}$ is from 0.05 to 1.5, $DS_{acetate}$ is from 0.05 to 2.5, and $DS_{propionate}$ is from 0.05 to 2.5.

10. The composition claim 1 wherein said dextran polymer derivative has a molecular weight ranging from 3000 daltons to 100,000 daltons.

11. The composition of claim 10 wherein said dextran polymer derivative has a molecular weight ranging from 3000 daltons to 70,000 daltons.

12. The composition of claim 1 wherein said composition is formulated for intravenous delivery.

13. The composition of claim 1 wherein said composition is formulated for ocular delivery.

14. The composition of claim 1 wherein said composition is formulated for delivery by inhalation.

15. The composition of claim 1 wherein:
(i) said dextran polymer derivative is dextran succinate and the $DS_{succinate}$ is from 0.5 to 2.5;
(ii) said dextran polymer derivative is dextran acetate succinate, the $DS_{succinate}$ is from 0.1 to 1.5, and $DS_{acetate}$ is from 1.0 to 2.3;
(iii) said dextran polymer derivative is dextran propionate succinate, the $DS_{succinate}$ is from 0.1 to 1.5, and $DS_{propionate}$ is from 0.25 to 2.0; or
(iv) said dextran polymer derivative is dextran acetate propionate succinate, the $DS_{succinate}$ is from 0.1 to 1.5, $DS_{acetate}$ is from 0.1 to 2.0, and $DS_{propionate}$ is from 0.1 to 2.0.

16. A pharmaceutical composition comprising:
a solid solution comprising
(a) from 0.01 to 99 wt % of an active agent, and
(b) from 1 to 99.99 wt % of a dextran polymer derivative comprising succinate groups and having a degree of substitution (DS) for succinate of at least 0.05,
wherein the dextran polymer derivative is selected from
dextran succinate,
dextran acetate succinate,
dextran propionate succinate,
dextran acetate propionate succinate, and
mixtures thereof, and wherein said dextran polymer derivative is water soluble above pH 5.

17. The pharmaceutical composition of claim 16 wherein the active agent is amorphous and is molecularly dispersed throughout the dextran polymer derivative.

18. The pharmaceutical composition of claim 16 wherein the composition is formulated for delivery by inhalation.

* * * * *